United States Patent [19]

Meadows

[11] Patent Number: 5,480,914
[45] Date of Patent: Jan. 2, 1996

[54] NONAQUEOUS THIXOTROPIC DRUG DELIVERY SUSPENSIONS AND METHODS OF THEIR USE

[75] Inventor: David L. Meadows, Mission Viejo, Calif.

[73] Assignee: Allergan, Inc., Irvine, Calif.

[21] Appl. No.: 238,947

[22] Filed: May 6, 1994

[51] Int. Cl.$^6$ .............................. A01N 29/00; A61K 31/02
[52] U.S. Cl. ...................... 514/743; 514/744; 514/745; 514/746; 514/747; 514/748; 514/749; 514/750; 514/751; 514/757; 514/759; 514/912
[58] Field of Search ................................ 514/743, 744, 514/745, 746, 747, 748, 749, 750, 751, 757, 759, 912

[56] References Cited

U.S. PATENT DOCUMENTS

| | | | |
|---|---|---|---|
| 3,911,138 | 10/1975 | Clark, Jr. | 424/352 |
| 3,962,439 | 6/1976 | Yokoyama et al. | 424/248 |
| 3,968,245 | 7/1976 | Higuchi | 424/330 |
| 3,989,843 | 11/1976 | Chabert et al. | 424/325 |
| 4,035,506 | 7/1977 | Lucas et al. | 424/303 |
| 4,105,798 | 8/1978 | Moore et al. | 424/352 |
| 4,115,544 | 9/1978 | Sheil | 424/14 |
| 4,168,308 | 9/1979 | Wretlind et al. | 424/244 |
| 4,366,169 | 12/1982 | White | 424/285 |
| 4,426,374 | 1/1984 | Wheeler | 424/60 |
| 4,452,818 | 6/1984 | Haidt | 424/352 |
| 4,490,351 | 12/1984 | Clark, Jr. | 424/5 |
| 4,649,047 | 3/1987 | Kaswan | 424/78 |
| 4,865,846 | 9/1989 | Kaufman | 424/428 |
| 4,882,150 | 11/1989 | Kaufman | 424/428 |
| 4,889,525 | 12/1989 | Yuhas et al. | 600/1 |
| 4,917,930 | 4/1990 | McCormick | 424/78 |
| 4,942,179 | 7/1990 | Borgarello et al. | 514/659 |
| 4,990,283 | 2/1991 | Visca et al. | 252/309 |

FOREIGN PATENT DOCUMENTS

| | | |
|---|---|---|
| 0091313 | 5/1983 | European Pat. Off. . |
| 0089815 | 9/1983 | European Pat. Off. . |
| 0288659 | 11/1988 | European Pat. Off. . |
| 0322249 | 6/1989 | European Pat. Off. . |
| 57-21312 | 2/1982 | Japan . |
| WO8100002 | 1/1981 | WIPO . |
| WO8400686 | 3/1984 | WIPO . |
| WO9118613 | 12/1991 | WIPO . |

OTHER PUBLICATIONS

G. Meseguer et al., "Gamma scintigraphic study of precorneal drainage . . . in rabbits . . . ," 1993, 95:229–234, *International Journal of Pharmaceuticals*.

G. R. Snibson et al., "Precorneal Residence Times of Sodium Hyaluronate Solutions Studied by Quantitative Gamma Scintigraphy," 1990, 4:594–602, *Eye*.

"CAB–O–SIL® TS–610 Treated Fumed Silica", Technical Data Sheet, Cabot Corporation, Tuscola, Ill., undated, 1 page.

"CAB–O–SIL® Fumed Silica Properties and Functions," undated, 33 pages.

"CAB–O–SIL® TS–530 Treated Fumed Silica", Technical Data sheet, Cabot Corporation, Tuscola, Ill., undated, 1 page.

"CAB–O–SIL® TS–720 Treated Fumed Silica", Technical Data Sheet, Cabot Corporation, Tuscola, Ill., undated, 1 page.

*Primary Examiner*—Nathan M. Nutter
*Attorney, Agent, or Firm*—Poms, Smith, Lande & Rose

[57] ABSTRACT

Nonaqueous thixotropic drug delivery vehicles for use in aqueous physiological systems are disclosed comprising a substantially homogeneous dispersion of at least one suspending aid in a nonaqueous perfluorocarbon or fluorinated silicone liquid carrier. Pharmaceutical compounds may be incorporated to provide thixotropic pharmaceutical compositions having improved delivery profiles and high drug localization. The thixotropic compositions act as free-flowing, drop-instillable liquids upon the application of stress yet behave as a visco-elastic material when at rest. Due to these thixotropic properties the pharmaceutical compositions have improved bioavailability, are capable of low dose volume delivery, and do not degrade the incorporated therapeutic or diagnostic compounds making them well suited for multi-dose packaging and administration.

10 Claims, 13 Drawing Sheets

NONAQUEOUS THIXOTROPIC DRUG DELIVERY SUSPENSIONS AND METHODS OF THEIR USE

FIELD OF THE INVENTION

The present invention relates in general to nonaqueous compositions intended for use in aqueous physiological systems. More particularly, the present invention is directed to thixotropic low volume, drop instillable drug delivery vehicles formed of one or more suspending aids dispersed in perfluorocarbon or fluorinated silicone liquids. These drug delivery vehicles may be combined with one or more pharmaceutical compounds to provide unexpectedly stable homogeneous pharmaceutical compositions possessing superior shelf lives, increased bioavailability, prolonged drug delivery profiles and advantageously small drop instaltation volumes.

BACKGROUND OF THE INVENTION

Pharmaceutical medicaments and diagnostic compounds are frequently incorporated into a delivery vehicle for administration to a targeted tissue site. Typically, drug delivery vehicles are formed as aqueous carriers, gels, polymeric inserts or particulates incorporating a pharmaceutical compound. Once the drug delivery vehicle is placed at the desired delivery site, the pharmaceutical compound is released from the delivery vehicle over a period of time. The time release profile of the drug is dependent upon a number of variables. Included in these variables are the release mechanisms of the drug from the drug delivery vehicle (typically either erosion, diffusion or both), the amount of drug incorporated into the drug delivery vehicle, the solubility of the drug in the surrounding physiological milieu and, in the case of particulate delivery vehicles, the particle size or size distribution of the vehicle.

Depending upon the physical characteristics of the vehicle itself as well as those at the intended target site, drug delivery vehicles may be delivered to the target site through a variety of known routes of administration. For example, aqueous based drug delivery solutions may be ingested, injected, inhaled, or applied directly to the skin or mucus membranes as drops, mists, sprays or the like. Conversely, gels and ointments are better suited to direct topical application due to their high viscosities which prevent drop elimination. Similarly, solid polymeric inserts must be physically inserted or affixed to the target site.

A particularly unique target site for pharmaceutical compounds is the ocular environment surrounding the surface of the eye. Aqueous solutions, gels and solid inserts have all been utilized to deliver ocular drugs as the controlled delivery characteristics of such known delivery vehicles make them well suited for such purposes. Though easily administered as drops, tear turnover and drainage through the lacrimal system quickly remove a major portion of any drop administered compound so that only a small fraction of the original dosage remains in the eye long enough to be of therapeutic impact. Moreover, the high liquid dose volumes inherent in water and oil based drop delivery systems result in inefficient use of the drug delivery compositions. As a result, repeated administrations of the drug containing drops are required to maintain an effective therapeutic level of the drug in the eye. To combat these drawbacks, pharmaceutical compositions formulated as ointments, gels or inserts have been developed which remain in the eye longer and gradually release their diagnostic or therapeutic drugs into the ocular environment in order to reduce the need for repeated administrations. However, these compounds are difficult to deliver and may affect the patient's vision.

More recently, particulate drug delivery systems relying on drug microparticles, microcapsules or drug-containing erodible microparticles or microcapsules have been developed with some limited success. These microparticles or microcapsules are designed to be suspended in a liquid carrier medium and delivered to the target tissue through injection, ingestion or as liquid drops. Once at the target site the microparticulates or microcapsules are intended to remain at that location after the liquid carrier has diffused or drained away. Typically, microparticulates are formed of a drug or drug containing polymer matrix comprising particles ranging from tens to hundreds of microns in diameter. The polymer matrix may be erodible to release the incorporated drug at the target site as the matrix gradually breaks down. Alternatively, the microparticulates may be formed of non-erodible polymers from which the incorporated drug simply diffuses out of and into the target tissue. Microcapsules are comparably sized hollow particles formed of a polymer shell encapsulating the desired pharmaceutical compound. The shell of microcapsules may also be composed of either erodible or nonerodible polymers. Problems with particulate settling during storage and with particle retention after delivery have limited the utility of such compositions.

The long term storage of any liquid pharmaceutical compound requires a liquid carrier medium that is physically and chemically compatible with the incorporated therapeutic or diagnostic compound, with any associated particulate carrier and with the intended physiological target environment. Generally, the liquid carrier of choice is a sterile water solution of the appropriate pH and osmolality. However, a problem with mixing and storing pharmaceutical compounds in aqueous carriers intended for an aqueous physiological target environment is that invariably the particles will break down or dissolve or the incorporated pharmaceutical compound will leach out into the aqueous carrier prior to administration. This may result in a significant loss of pharmaceutical activity following administration as any released or leached drug contained in the aqueous carrier will be flushed from the target site relatively rapidly as the carrier is drained through the lacrimal system.

This tendency to break down or leach into the carrier also limits the effective shelf-life of drug delivery vehicles based upon aqueous carriers. Depending upon the dissolution or diffusion rate of the incorporated pharmaceutical compound, the shelf-life will normally be much shorter than the preferred shelf-life. As a related problem, diffusion of the drug into the aqueous carrier makes it difficult, if not impossible, to formulate multiple dose packaging because uniform dose regimens cannot be ensured over time.

Adding to these problems, a significant number of the drugs and the polymeric microparticulates currently being used are hydrolytically labile. This characteristic is central to their ability to slowly dissolve or to release the drug into the target aqueous physiological environment. Because drugs or polymers exhibiting hydrolytic instability cannot be stored in aqueous vehicles, they must be stored in a dry state and suspended in the aqueous carrier immediately prior to their administration to the target site. This is a time consuming and burdensome inconvenience to the end user. Moreover, it requires specialized packaging designs which provide a method for separately storing the labile drug or polymer particles and the sterile carrier liquid in appropriate quantities. As a result, the package configuration must be limited to unit dose sizes with the attendant inconvenience and added costs.

Several nonaqueous liquid carriers have been utilized in the art in an attempt to address these problems. Among these are mineral oils, vegetable oils, silicone oils, and free fatty acids. Though generally effective for oral and dermal administration, when used in the ocular environment a significant disadvantage associated with these oils is that they combine with, and disrupt, the lipid layer of the tear film which, in turn, may cause the user to experience significant vision blurring and an unacceptable oily sensation. Even if the tear film is not disrupted, the significant difference between the refractive index of the tear film and that of the oil carrier causes vision blurring during the residence time of the oil in the eye.

A related drawback associated with the drop instillation delivery of ophthalmic pharmaceuticals in water or oil carriers is that conventional eye droppers have relatively limited delivery volumes restricted to drop sizes that may interfere with vision or be uncomfortable to the user. This is because the density and surface tension characteristics of the typical water- or oil-based systems do not allow for the practical delivery of drops having less than 35 µl volumes. Because the eye tear film can accommodate only about a 7 to 10 µl volume of liquid without disruption or discomfort, when amounts greater than this are delivered to the eye the excess liquid will either disrupt the tear film or be rapidly blinked away. This results in the inefficient and costly loss of both liquid carrier and pharmaceutical agent and still requires repeated drop administration over unacceptably short intervals for therapeutic effectiveness.

In an attempt to overcome the problems associated with conventional oil-based drug delivery vehicles, other nonaqueous liquids such as perfluorocarbons have been used as carries. For example, European patent application no. 0 091 313 discloses the use of perfluorocarbon-based pharmaceutical compositions as drug delivery vehicles. While a substantial improvement over traditional oil or water based carriers, pharmaceutical compounds suspended in perfluorocarbon carriers have been found to settle out over time leading to particulate aggregation and to uneven dispersion of the drug within the carrier. Though the uniform dispersion of the drug can usually be reestablished through shaking or mixing, prolonged and repeated aggregation of the drug particulates can, in some cases, reduce the efficacy of the pharmaceutical composition and adversely shorten the shelf life. Further, insufficient mixing of the particulates with the carrier prior to administration can result in a non-homogeneous suspension and inconsistent dosages.

Accordingly, it is an object of the present invention to provide nonaqueous drug delivery vehicles for the administration of therapeutic or diagnostic pharmaceutical compounds which provide for the prolonged homogeneous suspension and uniform dispersion of the incorporated compounds It is a further object of the present invention to provide effective high bioavailability pharmaceutical drug delivery compositions which promote the bioadhesion and retention of the incorporated drug onto the surface of the eye for extended periods.

It is yet a further object of the present invention to provide pharmaceutical compositions incorporating therapeutic or diagnostic pharmaceutical compounds which exhibit improved shelf lives and stability.

It is an additional object of the present invention to provide pharmaceutical compositions which may be administered to the eye using low dose volume drops, which remain in the eye as a comfortable, viscous composition.

It is yet an additional object of the present invention to provide pharmaceutical drug-delivery compositions for use in aqueous physiological systems which may be configured in multidose administration packaging.

It is yet another object of the present invention to provide pharmaceutical drug delivery compositions capable of forming drop sizes on the order of 10 µl when delivered from standard dropper bottles.

SUMMARY OF THE INVENTION

The present invention accomplishes these and other objectives by providing unique, nonaqueous thixotropic drug delivery vehicles formulated of one or more suspending aids dispersed in a fluorinated liquid carrier. These thixotropic vehicles may be combined with therapeutic or diagnostic compounds to provide stable compositions having extended shelf lives in conjunction with significantly improved bioavailability. Preferably, the compositions are formulated as substantially homogeneous suspensions which are conformationally stable to prevent settling out or separation of the incorporated particulate drugs or microparticulate carriers during prolonged storage. In addition to this conformational stability, the nonaqueous thixotropic drug delivery vehicles also prevent degradation of hydrolytically labile pharmaceutical compounds or, where present, hydrolytically labile polymer particulates. Due to their long term stability, the thixotropic pharmaceutical compositions of the present invention are particularly suitable for packaging in multidose configurations which provide efficient, low dose volume drug delivery characteristics.

As is known in the art, a thixotropic composition or compound is one that becomes fluid or less viscous when disturbed or shaken. When the internal shearing force is removed, the viscosity returns to its original "at-rest" value. Thus, in accordance with the teachings of the present invention, the disclosed thixotropic compositions are relatively viscous or gelatinous when in an undisturbed state yet are capable of liquid like drop instillation when exposed to the shearing forces associated with administration through a conventional dropper or needle like outlet. This at rest high viscosity maintains a substantially homogeneous dispersion of any pharmaceutical compound suspended in the drug delivery vehicles during storage. However, when stress is applied to the compositions such as during administration by drop instillation or other methods, the viscosities are greatly reduced, allowing the thixotropic compositions to act as free flowing liquids. In this low viscosity state, the thixotropic compositions behave similarly to the pure fluorinated liquid carrier allowing low dose volume drop instillation to be achieved. Following administration to the target site and removal of the dropping or delivery stress, the thixotropic compositions rapidly return to their original higher or "at-rest" viscosities.

In addition to providing a lubricating or wetting function, this rapid increase in viscosity following administration causes the compositions to behave as viscoelastic materials at the target site thereby confining any incorporated pharmaceutical compound or particulates at the target site. This previously unavailable confinement provides sharply enhanced bioavailability through a reduction in drug migration or drainage. In addition, the thixotropic compositions can alter the local environment of the target site by desiccating the surface of the tissue thereby promoting the adhesion and retention of any incorporated particulates. The resultant high localized bioavailability substantially reduces undesirable systemic side effects.

The thixotropic drug delivery vehicles of the present invention are preferably formed of a perfluorocarbon or fluorinated silicone liquid carrier, having at least one suspending aid dispersed therein. In general this suspending aid is any compound that assures the prolonged, uniform distribution of drug or polymer particulates incorporated in the liquid carrier. More specifically, the suspending aid may be any thickener, suspending agent or surfactant, which displays thixotropic properties when dispersed in a fluorinated liquid carrier. In a particularly preferred embodiment, this suspending aid is colloidal silicon dioxide or "CSD" and derivatives thereof.

In a another embodiment of the present invention, polymeric particulates may be added to the nonaqueous thixotropic compositions. Incorporated microparticulates may comprise a plurality of erodible particles or microcapsules. These microparticulates are uniformly dispersed throughout the drug delivery vehicle and may incorporate one or more pharmaceutical compounds.

A wide variety of polymers and pharmaceutical compounds can be used in forming the compositions of the present invention. Due to the nonaqueous character of the fluorinated liquid carriers utilized, they are particularly suitable for suspending microcapsules or microparticulates prepared with hydrolytically labile polymers or incorporating hydrolytically labile pharmaceutical compounds. However, pharmaceutical compositions comprising hydrolytically stable polymeric microparticulates or pharmaceuticals are also within the scope of the present invention. Further, those skilled in the art will appreciate that mixtures of differing erodible microparticulates or microcapsules can be combined in a single nonaqueous thixotropic composition to provide desirable polymer erosion rates, lubrication characteristics or drug release profiles.

In another aspect of the present invention, the dramatic reductions in composition viscosity resulting from the application of internal or external stress and shearing force, combined with the resultant physical properties of the fluorinated liquid carriers, provides a unique low drop volume administration capacity to the compositions. Unlike prior art aqueous and oil-based delivery systems, which are limited to a minimum drop sizes of about 35μl, the nonaqueous thixotropic compositions of the present invention form low volume doses of less than 10 μl. These low dosage volumes greatly reduce drug waste and undesirable side effects while enhancing the bioavailability of the pharmaceutical compound. Moreover, these low delivery volumes allow the thixotropic compositions to be readily introduced to the intended target sites through any available route of administration including ingestion, injection, inhalation, topical application, sprays, mists, drops and the like.

Another advantage of the compositions of the present invention is that they may be packaged and sterilized using conventional gamma irradiation techniques. Sterile fill procedures are also available as an alternative to radiation sterilizing techniques. The unique bacteriostatic properties of the nonaqueous liquids facilitates the formulation and utilization of multidose packaging by eliminating the necessity of preservative additives commonly used in the art. Additionally, the pharmaceutical compositions also can be configured for unit dose packaging if desired.

Other objects, features and advantages of the present invention will be apparent to those skilled in the art from a consideration of the following detailed description of preferred exemplary embodiments thereof taken in conjunction with the associated Figures which will first be described briefly.

BRIEF DESCRIPTION OF THE DRAWINGS

FIG. 1 is a graphical representation illustrating the effect of applied stress, plotted against the phase of the curve or delta, on five exemplary compositions of differing concentrations of CSD in perfluorodecalin where, as stress is applied, each composition reaches a point, marked by a sharp upturn in the curve, where it rapidly shifts from an elastic state to a viscous state;

FIG. 2 is a graphical representation illustrating the rapid reestablishment of elastic characteristics following the removal of stress on each composition for four exemplary compositions having differing concentrations of CSD in perfluorodecalin;

FIG. 3 is a graphical representation illustrating the recovery from a viscous state to an elastic state following the removal of stress for three exemplary concentrations of CSD in perfluorodecalin;

FIG. 4 is a graphical representation analogous to that of FIG. 3 for two additional exemplary compositions of CSD in perfluorodecalin;

FIG. 5 is a graphical representation of shear rate flow curves generated for five exemplary compositions having different concentrations of CSD in perfluorodecalin illustrating that the compositions behave as visco-elastic liquids as the shear rate increases;

FIG. 6 is a graphical representation of shear stress flow curves generated for five exemplary compositions having differing concentrations of CSD in perfluorodecalin showing the abrupt decrease in viscosity at well-defined stress thresholds for each composition;

FIG. 7 is a graphical representation of an accelerated stability profile comparing the degradation of a hydrolytically labile drug formulated in an aqueous solution versus an exemplary thixotropic pharmaceutical composition formulated in accordance with the teachings of the present invention;

FIG. 8 is a graphical representation of rabbit precorneal retention profiles for three sizes of nonerodible polymeric microparticulates administered using the nonaqueous delivery vehicles of the present invention; illustrating particulate bioadhesion and retention provided by the thixotropic compositions;

FIGS. 9A, 9B and 9C are comparative graphical representations showing the retention profiles of radiolabeled charcoal measured from three different areas of rabbit eyes following administration using a prior art aqueous delivery vehicle versus an exemplary nonaqueous thixotropic delivery vehicle of the present invention where FIG. 9A illustrates mean precorneal retention time of the labeled charcoal; FIG. 9B illustrates mean retention time measured at the inner canthus; and FIG. 9C illustrates the mean retention time measured in the lacrimal ducts of the same eyes;

FIGS. 10A, 10B, 10C, and 10D are sequential schematic representations of a rabbit eye and lacrimal system showing the retention of radiolabeled charcoal over time measured at intervals of 20 seconds, 50 seconds, 10; minutes and 38 minutes following administration of a prior art aqueous delivery vehicle;

FIGS. 11A, 11B, 11C, 11D and 11E are schematic representations of a rabbit eye and lacrimal system showing the retention of radiolabeled charcoal over time measured at intervals of 50 seconds, 10 minutes, 19 minutes, 34 minutes and 135 minutes following administration of an exemplary nonaqueous thixotropic delivery vehicle;

FIGS. 12A and 12B are comparative graphical representations of the effects of varying amounts of pilocarpine administered using prior art delivery vehicles; FIG. 12A shows the mean change in rabbit pupil diameter over time following the administration of three different concentrations of pilocarpine using a nonaqueous delivery vehicle of the present invention; FIG. 12B shows the mean change in rabbit pupil diameter over time following the administration of three different concentrations of pilocarpine using a prior art aqueous delivery vehicle;

FIGS. 13A and 13B are comparative graphical representations of heart rate responses of glaucomatous monkeys to a single topical application of levo-bunolol using prior art delivery vehicles versus those of the present invention; FIG. 13A shows the undesirable decrease in heart rate upon administration and migration of levo-bunolol using a prior art aqueous delivery vehicle; FIG. 13B shows the heart rate response following administration and retention of levo-bunolol using an exemplary nonaqueous delivery vehicle of the present invention;

FIGS. 14A and 14B are comparative graphical representations of changes in intraocular pressure to a unilateral topical application of brimonidine using undesirable prior art delivery vehicles versus those of the present invention; FIG. 14A shows the undesirable pressure reduction in untreated eyes following administration and migration of the drug in the prior art aqueous solution; FIG. 14B shows the significant lower decrease in intraocular pressure in the untreated eyes following administration and retention of the drug in an exemplary nonaqueous composition of the present invention.

DETAILED DESCRIPTION OF EXEMPLARY EMBODIMENTS

Figure 1:
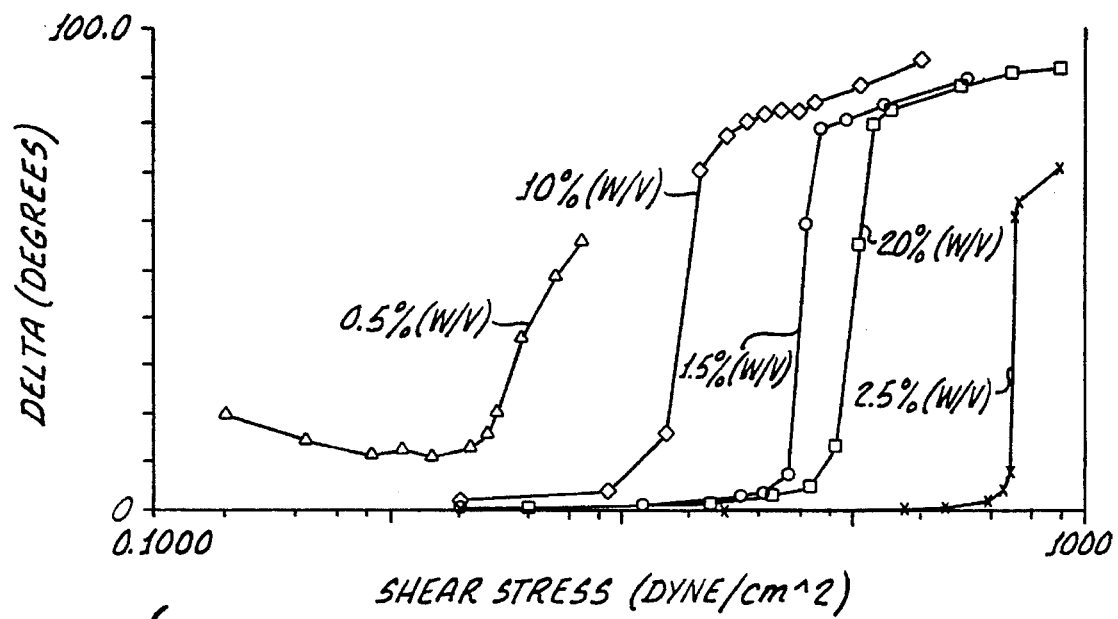

In a broad aspect, the stable nonaqueous thixotropic drug delivery vehicles of the present invention comprise one or more suspending aids dispersed in a perfluorocarbon or fluorinated silicone liquid carrier. These delivery vehicles may be combined with one or more therapeutic or diagnostic compounds to form thixotropic pharmaceutical compositions that are substantially homogeneous and capable of low volume drop installation. The suspended pharmaceutical compound may be in a particulate salt form or associated with polymer microparticulate or microcapsule carriers.

Because of the bacteriostatic, nonirritating, and in fact, soothing and lubricating properties of the fluorinated liquid carriers, the thixotropic compositions formed in accordance with the teachings of the present invention are particularly well suited for use in connection with the diagnosis or treatment of injuries or diseases of the eye. Further advantages associated with their ophthalmic utility are multi and unit dose capability as well as the low surface tension and high density of the nonaqueous liquid carriers which allow for small volume drop delivery. However, those skilled in the art will appreciate that the nonaqueous thixotropic compositions of the present invention are equally well suited for use in applications to other physiological environments where the repeated or prolonged administration of a pharmaceutical compound to sensitive tissue is desired.

Accordingly, for purposes of explanation and without limiting the scope of the present invention, where appropriate the following exemplary embodiments will be discussed in the general context of ophthalmic pharmaceutical compositions utilized for the treatment of ocular injuries and diseases. However, it should be emphasized that the thixotropic compositions may be introduced to a variety of target sites through all common routes of administration such as oral, dermal, injection, intravenous, nasal as well as others known in the art.

Exemplary perfluorocarbons which may be used as nonaqueous liquid carriers in the low volume, highly stable thixotropic compositions of the present invention include perfluorocyclocarbons, acyclic perfluorocarbons and their derivatives. As known in the art, exemplary perfluorocarbon derivatives are typically nitrogen and oxygen containing compounds such as amines and ethers. Preferably, the nonaqueous liquid carrier compounds are perfluorinated, meaning that all of the hydrogens bonded to the carbons of the compound are substituted with fluorine. Thus, perfluorinated cyclic and acyclic hydrocarbons as well as the amine and ether derivatives of these compounds are preferred for utilization in the pharmaceutical compositions of the present invention.

Exemplary perfluorocarbons which are particularly suitable for use in the nonaqueous thixotropic drug delivery vehicles of the present invention are blood substitutes. Perfluorocyclocarbon blood substitutes include perfluoroperhydrophenanthrene, perfluoromethylcyclohexane, perfluoro(1,3-dimethylcyclohexane), perfluorotrimethylcyclohexane, perfluoroisopropylcyclohexane, perfluoroendotetrahydrodicyclopentadiene, perfluoro-1-methyl-4-isopropylcyclohexane, perfluoro-1-methyl-4-isopropylcyclohexane, perfluoro-n-butylcyclohexane, perfluoro(decahydronaphthalene), perfluoro(decahydro-1-methylnaphthalene), perfluoro(decahydrodimethylnaphthalene), perfluoromethyladamantane, perfluorotrimethylbicyclo(3.3.1.)nonane, and perfluorodimethylbicyclo(3.3.1)nonane. Oxygen and nitrogen containing derivatives of perfluorocarbons which may be used as liquid carriers include perfluorotributylamine, perfluorotriisopropylamine, perfluorotetrahydrofuran and perfluoroethers.

Exemplary fluorinated silicone oils for use in practicing the invention are the polyalkylfluoroalkylmethylsiloxanes. In particular, the polytrifluoropropylmethylsiloxanes with molecular weights of between 500 and 14,000 are suitable for use in the thixotropic pharmaceutical compositions of the present invention.

Preferred perfluorocarbons and fluorinated silicones have vapor pressures sufficiently low to prevent significant liquid loss caused by their evaporation from containers during storage. Fluorinated liquid carriers having ambient pressure boiling points greater than 100° C. are preferred to ensure that any evaporative losses are less than that observed for water. Additionally, it is preferred that exemplary perfluorocarbons and fluorinated silicones are eliminated relatively quickly from the body. Less desirable perfluorocarbons are known to reside in fat tissues for as long as 2–3 years. Perfluoro(decahydronaphthalene), also referred to as "PFD," and perfluoroperhydrophenanthrene, commonly referred to as "PPP," are preferred perfluorocarbons because of their relatively high ambient pressure boiling points of 142° C. and 215° C., respectively. Additionally, PFD and PPP are eliminated from the body relatively rapidly when systemically administered. For example, following systemic administration the half-life of PFD in the body is approximately seven days.

An additional aspect of the present invention is the dispersing or blending of one or more aids in the perfluorocarbon or fluorinated silicone liquid carrier. Surprisingly, it appears that the substantially homogeneous dispersion of the suspending aid in the carrier imparts the thixotropic properties in the compositions of the present invention.

Accordingly, any suspending aid compound which may be administered to a physiological target site, providing the appropriate thixotropic characteristics and compatible with the fluorinated liquid carrier may be used to practice the present invention. Exemplary suspending aids include fumed silica and related materials as well as commercially available surfactants, dispersants, suspending agents and excipients. Which suspending aids are used can be determined utilizing routine testing procedures and will, to some extent, be dependent upon the selected pharmaceutical compound, fluorinated liquid carrier and method of administration.

While a number of commercially available suspending aids can produce some measure of thixotropic characteristics in nonaqueous fluorinated liquid carriers, colloidal silicon dioxide (CSD) and derivatives thereof are particularly well-suited for use in the compositions of the present invention. In addition to being approved for pharmaceutical uses by the United States Food and Drug Administration, colloidal silicon dioxide is relatively inexpensive and does not require specialized handling or storage techniques.

Colloidal silicon dioxide or CSD, sold under the trade name Cab-o-sil® (Cabot, Inc.), is a fine particulate material having a relatively high surface area to weight ratio. Several different derivatives of CSD, each treated with distinct chemical compounds during production to modify their surface properties, are commercially available. Generally, CSD particulates and derivatives thereof are branched chain aggregates having maximum lengths of a few tenths of a micron and surface areas ranging from 100 to 400 square meters per gram. Chemical groups occurring on the surface of the CSD particles include siloxanes and hydroxyls in addition to various derivative specific chemical moieties added by post production processing. The polar hydroxyl groups, both isolated and hydrogen bonded, are hydrophilic in nature and render unmodified CSD particles slightly hygroscopic.

Specifically, the silanol groups present on the surface of the CSD may be chemically modified using a number of different agents such as halosilanes, alkoxysilanes, silazanes and siloxanes. In contrast to the starting material, CSD modified in this way tends to be hydrophobic to some extent. Yet, while the surface properties of the CSD have been altered, the material still retains the capability to form thixotropic compositions. Accordingly, it is within the scope of the invention to use these derivatives of colloidal silicon dioxide as thixotropic agents either alone or in combination with the underivatised CSD. In the following discussion the terms CSD and colloidal silicon dioxide will refer to the underivatised material unless otherwise specified.

Without wishing to be bound by any one particular theory of operation, it is believed that the presence of polar hydroxyl groups on the surface of the colloidal silicon dioxide promotes the hydrogen bonding of the CSD particles rendering low hydrogen bonding and nonhydrogen bonding liquid systems thixotropic. Different grades or derivatives of CSD may be used in accordance with the teachings of the present invention to provide thixotropic compositions with desired properties. More particularly, when CSD particles are dispersed in a nonhydrogen bonding liquid system, such as the fluorinated liquid carriers of the present invention, it is believed that a three-dimensional network structure of CSD particles are formed. Network formation produces an increase in the viscosity of the system whenever it is at rest. When the network is temporarily disrupted or fragmented such as during an application of shear or stress on the system, the real and apparent viscosities decrease in proportion to the increased speed of the shear rate or to the length of time at a constant speed shear rate. Upon the cessation of the shear force, the viscosity approaches its original "at rest" value as the CSD particles, having no competition for the bonding sites on their surface in the nonaqueous fluorinated carrier, reform the three-dimensional network.

This lack of competition is due to the substitution of fluorine for the carbon-bound hydrogen of the nonaqueous liquid carriers. As the fluorine-carbon bond is stronger than a carbon-hydrogen bond, the CSD-bound hydrogen will not displace the fluorine on the liquid carrier. Under such conditions, the CSD particles rapidly orient themselves in the liquid to form hydrogen bonds, thereby lowering the overall energy of the system. The number of bonds formed naturally approaches the maximum number possible for the selected concentration of CSD providing a sharp increase in viscosity.

It is in nonhydrogen bonding systems, such as the fluorinated liquid carriers of the present invention, that CSD particles display their greatest efficiency in network formation and provide the greatest viscosity increase. In such nonhydrogen bonding systems, the concentration of CSD particles is an important determinant of the degree of network formation. With respect to the present invention, CSD concentrations between about 0.01% w/v to about 20% w/v may be used to provide stable thixotropic compositions having low drop volume instillation capability. More preferably, the thixotropic drug delivery vehicles and pharmaceutical composition of the present invention may be formed using CSD concentrations of between 0.05% w/v and 10% w/v. The amount of CSD used may be specifically selected to adjust the "at rest" viscosity of the system and to alter drug retention and delivery profiles where desired. The exact concentration of CSD used in any particular embodiment is dependent upon several factors, including the expected method of administration, the nature and amount of any incorporated drug, storage conditions, and the precise characteristics of the selected nonaqueous liquid carrier.

Another factor in determining the degree of network formation in the compositions of the present invention is the degree of dispersion of the CSD particles in the nonaqueous liquid carrier. The optimum dispersion of the CSD particles is largely dependent on the grade and concentration of CSD used, the properties of the nonaqueous liquid carrier, and the viscosity desired. The amount of dispersion required may be determined experimentally using techniques well-known in the art.

The following nonlimiting examples of various exemplary formulations of the compositions of the present invention illustrate exemplary methods for their formation and their resultant thixotropic characteristics.

EXAMPLE 1

A series of formulations containing colloidal silicon dioxide (CSD) dispersed in perfluorodecalin was prepared for characterization by rheometry. The concentration of CSD in perfluorodecalin ranged from 2.5% w/v to 0% w/v in 0.5% w/v increments. More specifically, a 2.5% w/v stock dispersion of CSD in perfluorodecalin was prepared by mixing CSD (Cabot, Inc.) in perfluorodecalin (Air Products Corp.) at approximately 1600 rpm for 20 min. A Talboys Model 134-2 with a Lightman® Model R500 high shear impeller was used to disperse the CSD. At 20 minutes, no clumps were observed, and the Hegman grind was greater than 8.

Dilutions in 0.5% w/v increments from 0.5% w/v to 2% w/v were made by adding a weighted amount of perfluorodecalin. The dilute batches were mixed by hand until an even suspension was obtained. No separation or settling of these preparations was observed over time.

EXAMPLE 2

In order to determine the stress threshold at which the CSD network collapsed, stress sweeps were run on the five dispersions formulated in Example 1. The stress sweeps were conducted using a Carri-med and CNMR CS 100 rheometer with an optical encoder upgrade. The measuring geometry for all the CSD/perfluorodecalin dispersions was a 4 cm SS Flat Plate with solvent trap. The gap, selected after conducting probe studies using the 2.5% w/v CSD/perfluorodecalin dispersion, was set at 250 µm for the stress sweeps. The measuring geometry for perfluorodecalin was a recessed concentric cylinder and cup set at a 4 mm gap. These stress studies were run at 15° C. to minimize the evaporation of perfluorodecalin. For longer experiments (greater than 10 minutes), a cover was placed over the Flat Plate to prevent perfluorodecalin vaporization. FIG. 1 plots delta versus shear stress for each of the dispersions. Delta is the phase of the actual curve relative to the applied sinusoidal stress. If the material is in phase, a delta of zero is observed implying that the dispersion is purely elastic while a delta of 90° indicates that the dispersion is out of phase and purely viscous. FIG. 1 shows that for each dispersion, the delta goes from $\leq 10°$ to $\geq 60°$ at a well-defined stress threshold. This stress threshold is CSD concentration dependent and indicates the presence of an elastic three-dimensional network at low or resting stresses (i.e. low delta values). At the point when sufficient stress is applied, for instance during administration of a drug, the three-dimensional network is broken, and the thixotropic composition acts as a free-flowing liquid, represented here by a high delta value.

EXAMPLE 3

Figure 2:
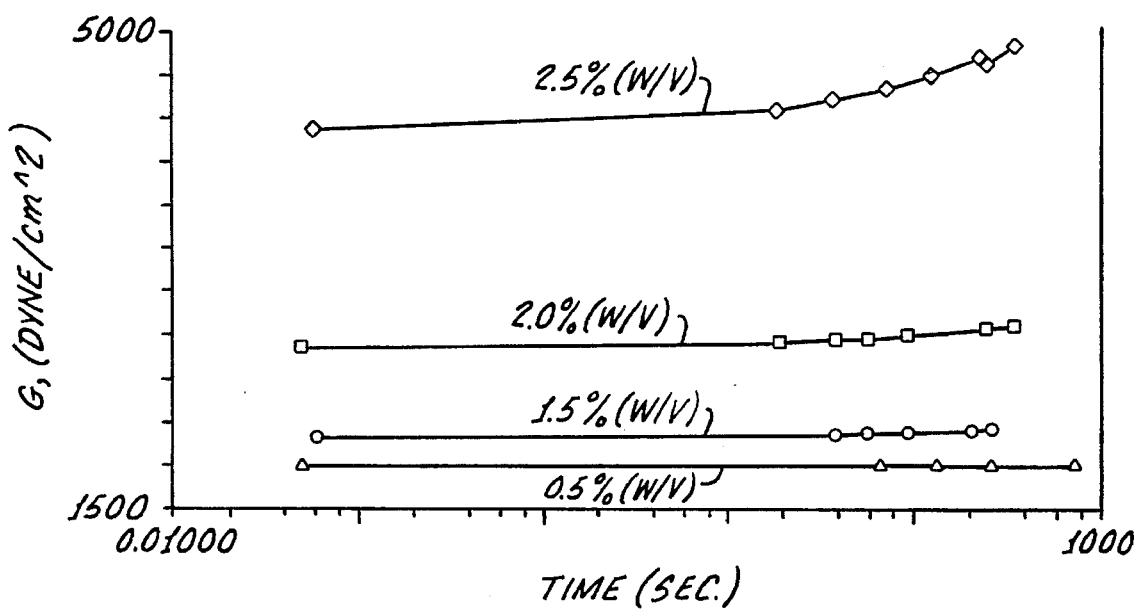

Studies were also conducted to determine the amount of time required for the CSD three-dimensional network to reform after being broken down by high, flowing pre-shear stresses. The storage modulus G' was monitored over time at fixed, low stresses and frequencies for each dispersion. G' is a measure of the elasticity of the materials and is directly related to the formation of the three-dimensional network of dispersed CSD and perfluorodecalin. The dispersions of Example 1 were used with the measuring protocols described in Example 2. Immediately following a pre-shear stress, designed to disrupt the three-dimensional CSD network, the oscillation run commenced with the first data points obtained within 0.4 to 0.8 seconds after removal of the stress. The results, shown in FIG. 2, indicate that for all dispersions, the elastic three-dimensional network was reformed almost instantly. No time lapse was detected using the study protocol.

EXAMPLE 4

Figure 3:
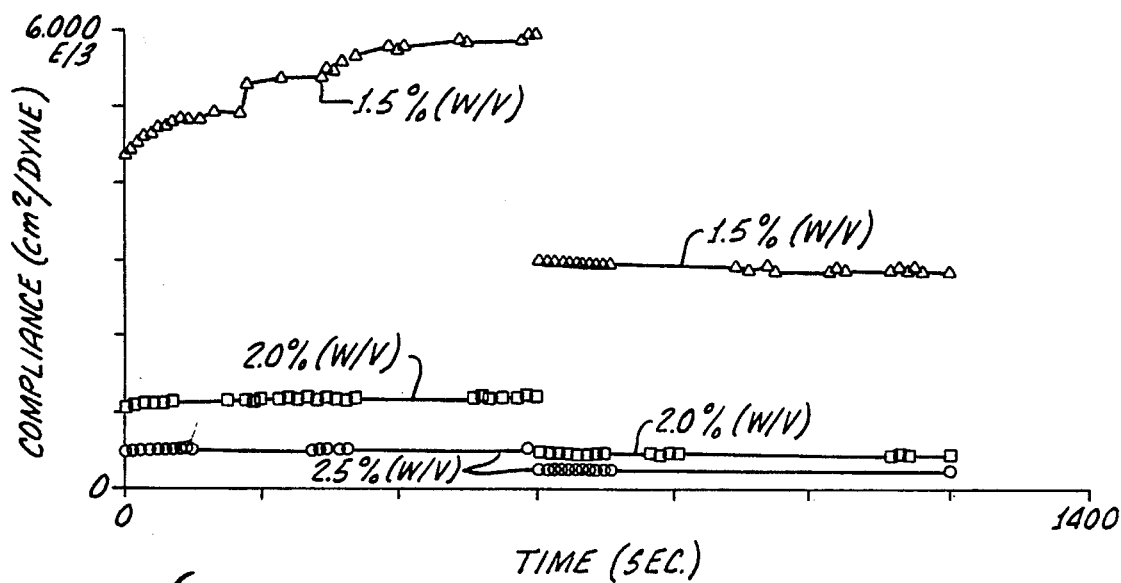
Figure 4:
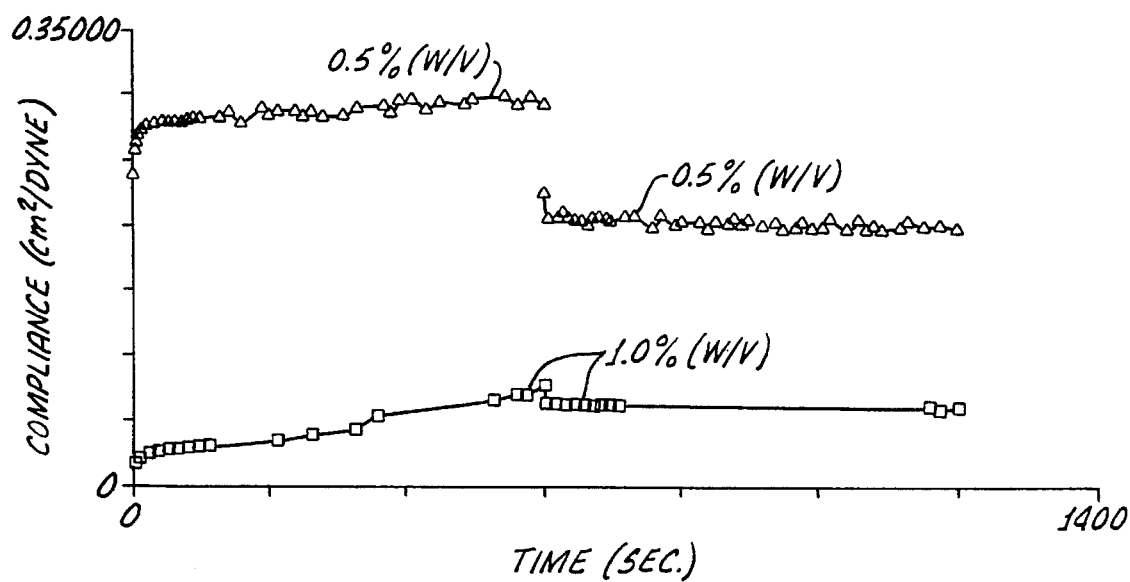

Creep studies were conducted on the dispersions formulated in Example 1 using the measurement protocols of Example 2. Low constant stresses were applied for 10 minutes; then the stresses were removed and the individual dispersions were monitored for an additional 10 minutes. Compliance (strain/stress) versus time was plotted for each dispersion giving the results shown in FIGS. 3 and 4. Specifically the results for formulations of 1.5%, 2% and 2.5% w/v CSD are shown in FIG. 3 while the results for formulations of 0.5% and 1% w/v CSD are shown in FIG. 4. Under applied stress, the material instantly deformed and remained in the same state as long as the stress was present. Upon removal of the stress, the three-dimensional CSD matrix was rapidly reestablished and the dispersions returned to their original resting viscosity which also remained constant over time. This effect was more pronounced for the dispersions having $\geq 1.5\%$ w/v CSD while, as expected, the 0.5% and 1.0% w/v dispersions exhibited a more fluid behavior. These results, using long periods of applied stress, also indicate that the three-dimensional network will reestablish itself over a prolonged period and repeated disruption.

EXAMPLE 5

Figure 5:
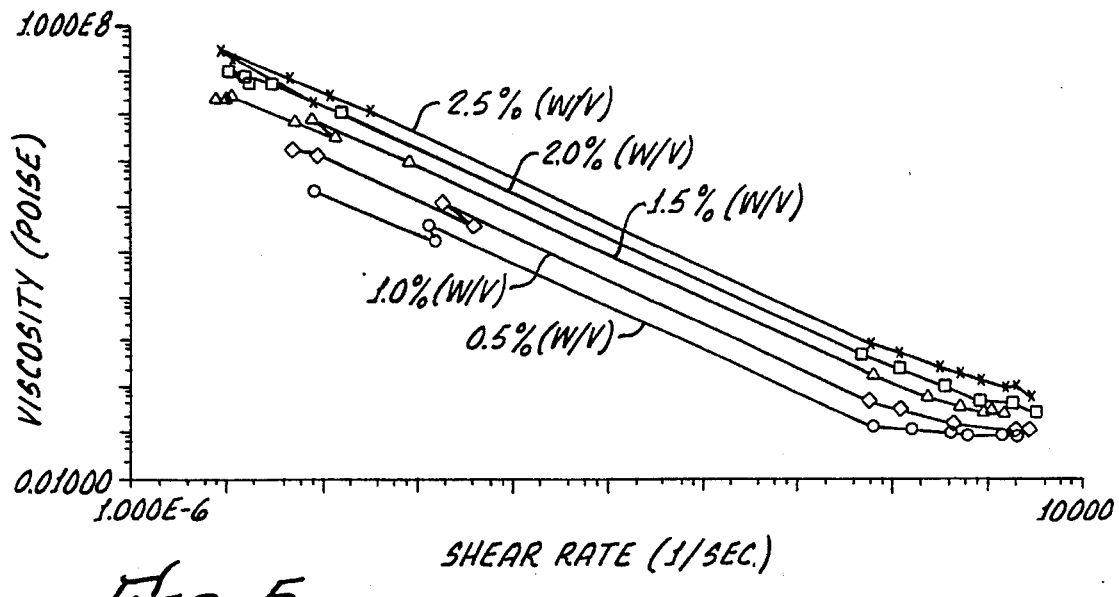
Figure 6:
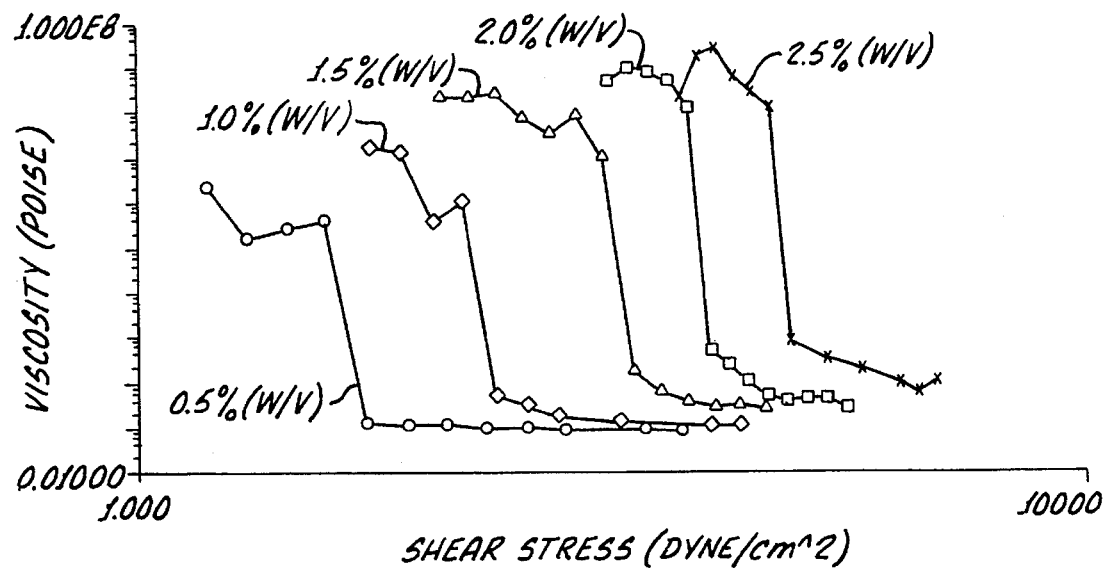

To further characterize the rheology of the dispersions formulated in Example 1, complete flow curves, fit to the Cross model, were generated over a broad range of shear rates. The Cross model, fitted to each flow curve, indicated that both the high and low shear rate Newtonian and power regions were acquired. The results are shown in FIGS. 5 and 6 and Table 1 immediately below. FIG. 5 plots the log viscosity versus the log shear rate and produces typical flow curves despite somewhat erratic data at low shear rates. FIG. 6 plots the log viscosity versus log shear stress. The transition from strain (nonflow) to shear rate measurements are indicated by the almost instantaneous decrease in viscosity between two stresses for each dispersion. The inflection point for each dispersion shown in FIG. 6 depicts the approximate yield stress or point where the three-dimensional CSD network collapsed. As expected, the yield stress increases with increasing CSD concentration. Table 1 below summarizes the important viscosity data obtained from the flow curves and the fitted Cross model. Zero and infinite rate viscosities of Table 1 were obtained from the Cross model equation. Yield stresses were calculated from flow curve data.

TABLE 1

| SUMMARY OF FLOW CURVE ANALYSIS | | | |
| --- | --- | --- | --- |
| Concentration of CSD in PFD [%(w/v)] | Zero Rate Viscosity [poise] | Infinite Rate Viscosity [poise] | Yield Stress [dynes*cm$^{-2}$] |
| 2.5 | $1.311 \times 10^8$ | 0.48 | 533.0 |
| 2.0 | $2.371 \times 10^7$ | 0.25 | 238.2 |
| 1.5 | $4.146 \times 10^6$ | 0.20 | 108.9 |
| 1.0 | $4.146 \times 10^6$ | 0.11 | 28.5 |
| 0.5 | $3.746 \times 10^5$ | 0.09 | 8.5 |
| 0 | Newtonian viscosity, 0.092 poise | | |

Those skilled in the art will appreciate that Table 1 dramatically illustrates the principles of the present invention. When the three-dimensional CSD network is intact (at Zero Rate Viscosity) the gel-like viscosity of the thixotropic compositions ranges from approximately $3.7 \times 10^7$ centipoise to $1.311 \times 10^{10}$ centipoise depending on the concentration of colloidal silicon dioxide. Yet, when stress is applied, and the CSD network is disrupted (at Infinite Rate Viscosity), these same thixotropic compositions exhibit free-flowing viscosities ranging from only approximately 9 centipoise to 48 centipoise. Significantly, as the CSD concentrations drop, these Infinite Rate Viscosities approach the 9.2 centipoise viscosity observed for pure perfluorodecalin without CSD and act as freeflowing Newtonian fluids. Accordingly, as dramatically demonstrated by the data above, when the CSD network is disrupted through the application of stress, the thixotropic compositions of the present invention behave remarkably like pure perfluorodecalin in terms of flow characteristics and drop installation capability.

This rheological data further demonstrates that fully dispersed CSD/perfluorodecalin suspensions exist in a highly elastic state at resting shear stresses or, more specifically, at normal gravitational stresses. Increasing stresses to a threshold level, i.e., by drop administering the composition to a physiological target site, results in a rapid collapse of the visco-elastic three-dimensional CSD network leaving the thixotropic drug delivery vehicle to act as a free-flowing liquid. However, the three-dimensional CSD network appears to re-form within a very short period following the removal of the stress. This rapid restructuring is important in maintaining a homogeneous suspension and uniform dispersion of an incorporated pharmaceutical compound over a prolonged storage period and after repeated shaking during administration. Further, the rapid reestablishment of the CSD network significantly enhances the retention of incorporated drugs at the target site thereby increasing bioavailability and reducing systemic side effects associated with migration of the administered drug from the target site. These examples also show that the amount of stress required to collapse the three-dimensional CSD network is dependent on the concentration of CSD in the nonaqueous liquid carrier.

In addition to providing the surprisingly dynamic rheological properties illustrated above, the thixotropic compositions of the present invention are extremely bio-compatible as illustrated by the following nonlimiting example of non-toxicity.

EXAMPLE 6

The non-toxic nature of the thixotropic drug delivery vehicles of the present invention was demonstrated by administering various concentrations of colloidal silicon dioxide in perfluorodecalin to the eyes of eight female New Zealand albino rabbits. More specifically, CSD dispersions of 2% w/v, 1% w/v and 0.5% w/v were prepared as in Example 1 and topically administered to the rabbits six times, at one hour intervals. Dose volumes of 8 μl were used for each dispersion along with a perfluorodecalin control. Following the six topical installations, each of the eyes was subjected to gross and slit lamp examination. These examinations showed that the 1% w/v and 2% w/v CSD dispersions in perfluorodecalin were slightly discomforting to the eye, but nonirritating to the conjunctiva and nontoxic to the cornea. Further, the 0.5% w/v CSD dispersion and the pure perfluorodecalin produced no discomfort, irritation, or toxicity in any of the rabbits studied. This lack of toxicity shows that the thixotropic drug delivery vehicles of the present invention can be administered repeatedly over a prolonged period without causing discomfort or endangering the health of the subject.

Another aspect of the invention involves incorporating at least one wetting agent or pharmaceutical compound in the nonaqueous thixotropic drug delivery vehicles. As previously indicated, any pharmaceutical compound may be incorporated in its particulate salt form or associated with a polymeric particulate carrier. Further, those skilled in the art will appreciate that the hydrolytic properties of the desired pharmaceutical compound or any associated polymeric particulate may be selected to enhance bioadhesion or drug stability. Exemplary wetting agents are hydrolytically active polymeric compounds, usually in particulate form, which facilitate the retention of fluid at the target site through the absorption and subsequent slow release of natural tear fluid. In either case, the incorporated wetting agent or pharmaceutical compound is preferably mixed to form a homogeneous dispersion within the fluorinated liquid carrier.

The polymeric particulate or pharmaceutical compound incorporated in the thixotropic compositions may be selected or modified to produce a wide variety of desired delivery profiles. Specifically, the hydrolytic properties of the incorporated agents may be adjusted to provide for their sustained dissolution in the aqueous environment of the eye. This is easily accomplished by selecting different salts of the drug or by associating it with a hydrolytically resistant polymer. It should be emphasized that the use of such hydrolytically stable particulates with prior art aqueous or oil delivery vehicles is inefficient as these particulates are quickly flushed from the target site following administration, leading to low drug bioavailability at the target site and to enhanced side effects. Yet, the thixotropic characteristics provided by the compositions of the present invention promote the retention of these particulates at the target site. Further, the thixotropic compositions can alter the aqueous environment of the target site through partial desiccation, significantly enhancing the bioadhesion of any incorporated particulates. Accordingly, the compositions of the present invention provide for the sustained dissolution of hydrolytically resistent particulates at the target site allowing for relatively higher bioavailability and prolonged delivery profiles.

More specifically, when CSD/perfluorodecalin suspensions are administered to the eye, the CSD is found to desiccate the much in layer of the eye and to stick to the cornea to some extent as a result. This alters the surface adhesion properties of the eye and promotes the bioadhesion and retention of any incorporated particulates. Further, it slows the erosion or dissolution of hydrolytically labile drugs or polymers present, thereby modifying their release and dosing profiles. Accordingly, if desired, it is possible to change the solubility or hydrophobicity of the selected pharmaceutical compounds to take advantage of these effects. By changing the salt form of the drug or by associating it with a more hydrophobic microparticulate, the delivery characteristics of the drug can be enhanced. Accordingly, it is well within the scope of the present invention to use the nonaqueous thixotropic delivery vehicles to intensify the dosing characteristics of previously inefficient forms of selected pharmaceutical compounds by modifying the physiological target site.

These same characteristics may also be used to provide thixotropic compositions useful for the prolonged lubrication or wetting of the physiological target site. In these compositions, one or more types of hydrolytically active polymer particulates are added to the nonaqueous thixotropic delivery vehicles. Following administration, the particulates are retained at the target site and provide for the sustained delivery of absorbed tear fluid or other liquids. Such compositions are particularly effective in the treatment of "dry eye" and related disorders.

Exemplary polymers which provide suitable wetting agents comprise poly(methylvinylether/maleic anhydride), carboxy vinyl polymers, polyfumaric acid/sebacic acid, collagen, gelatin, polyvinyl alcohol, methylcelluloses, polyorthoesters, polyglycolic acid, polylactic acid, polyvinylpyrrolidone, polysebacic acid anhydride, polycarboxyphenoxypropane anhydride, polyterephthalic acid anhydride, and polyphosphazine. A preferred exemplary polymer is Gantrez AN, a Poly(methylvinylether/maleic anhydride) available from GAF. Particulates made from this polymer provide a long shelf life, do not prematurely erode and are very effective when delivered to the aqueous target environment.

Although it is possible to use the thixotropic vehicles of the present invention in pure form or with a wetting agent, preferably a pharmaceutically effective amount of at least one compound can be incorporated. Specifically, the thixotropic compositions can be modified to include from approximately 0.001% to 50% w/v of a therapeutic or diagnostic compound when used for drug administration. The precise amount of pharmaceutical compound incorporated in the thixotropic compositions of the present invention is dependent upon the compound of choice, the required dose, and the form of the drug actually combined with the thixotropic drug delivery vehicle. Those skilled in the art will appreciate that such determinations may be made by using well-known techniques in combination with the teachings of the present invention.

Any pharmaceutical therapeutic or diagnostic compound which is compatible with the selected nonaqueous liquid carriers and suspending aids may be incorporated in the thixotropic drug delivery vehicles. Exemplary pharmaceutical compounds included protein growth factors, oligopeptides, antibacterial, antihistaminic, anti-inflammatory, miotic, anticholinergic, mydriatic, antiglaucoma, antiparasitic, antiviral, carbonic anhydrase inhibitor, antifungal, anesthetic, diagnostic and immunosuppressive agents. Preferred pharmaceutical compounds for use in ocular situations include epithelial growth factor, levobunolol hydrochloride, UK-14304-18, pilocarpine, dipivefrin (DPE), sodium fluorescein, tetracycline, chlortetracycline, bacitracin, neomycin, polymyxin, gramicidin, tobramycin, ciprofloxacin, norfloxacin, penicillin, erythromycin, cefazolin, ceftazidime, imipenem, idoxuridine, hydrocortisones, dexamethasone, dexamethasone 21 phosphate, fluocinolone, medrysone, prednisolone acetate, fluormetholone, betamethasone, phenylephrine, eserine salicylate, carbachol, echothiophate iodide, demecarium bromide, cyclopentolate, isopilocarpine lactam, homatropine, scopolamine, epinephrine, ibuprofen, aceclidine, teretinoin, and pirenoxine. In accordance with the present invention, various salt forms of these compounds may be used to modify the release profile of the pharmaceutically active agents.

Just as importantly, the stability of the nonaqueous thixotropic compositions of the present invention allows for the direct administration of prodrug forms of the selected pharmaceutical compounds to the desired target site. The administration of these highly unstable, hydrolytically labile pharmaceutical compounds has essentially been impossible using the prior art oil or water delivery vehicles. However, the thixotropic properties and nonreactive nature of the compositions of the present invention maintain the potency of the prodrugs during storage. This in turn, allows the delivery of a generally more efficacious form of the drug to the target site where they are activated by the aqueous environment.

It is also contemplated as being within the scope of the present invention to associate the selected pharmaceutical compounds with bioerodible microparticulates or microcapsules prior to dispersion in the thixotropic drug delivery vehicles. Besides the hydrolytically active polymeric compounds which may also be used as wetting agents, the selected drugs can be combined with hydrolytically stable polymers. Exemplary hydrolytically stable polymers which are suitable for use in the thixotropic drug delivery vehicles include acrylate, ethylene vinylacetate, silicones, polyurethanes, and polysulfones. Preferably, the polymeric microparticulates are sized on the order of approximately 2 µm to 200 µm, while the microcapsules are sized on the order of approximately 20 µm to 200 µm.

Moreover, it is also within the scope of the present invention to prepare thixotropic pharmaceutical compositions comprising a mixture of particle sizes or mixtures of microcapsules and microparticulates with varying erosion rates or hydrophobicity profiles. Such combinations can be designed to provide specific drug release profiles, including high initial concentrations or socalled zero order deliveries which may be used to provide combinations of different pharmaceutical compounds. However, those skilled in the art will appreciate that particulates or microcapsules prepared from polymers which are hydrolytically labile are particularly well suited for use with the perfluorocarbons or fluorinated silicone carriers of the present invention as they are stable in solution yet will erode in the aqueous environment of the target site thereby eliminating themselves from the site.

An alternative hydrolytically labile microparticulate can be formed from those compounds which have ionic side chains capable of complexing with a drug of opposite ionic charge. Microparticulates formed of these polymers erode in the aqueous physiological environment and dissociate the drug which is ionically bound to the polymer thereby delivering the drug to the target site. Thixotropic pharmaceutical compositions prepared with these ionic polymers suspended in a nonaqueous carrier such as perfluorocarbon do not prematurely release the ionically bound drug and therefore can be prepared in stable, multidose forms.

Advantageously, the nonaqueous liquid carriers utilized to form the low volume thixotropic pharmaceutical compositions of the present invention are soothing, nonirritating and nontoxic. Thus, their use in physiological applications, and in particular the ocular environment, is particularly desirable. The following nonlimiting examples further illustrate and confirm the nontoxic utility of exemplary pharmaceutical compositions of the present invention.

EXAMPLE 7

To demonstrate the nonirritating characteristics of the thixotropic pharmaceutical compositions of the present invention, ocular toxicology studies were performed on New Zealand albino rabbits. Different concentrations of AGN 191053, a prodrug of isopilocarpine lactam which is unstable in an aqueous environment, were topically administered to the rabbit eyes six times in one day at one hour intervals. More particularly, concentrations of 0.3%, 0.5% and 1% w/v AGN 191053 were combined with perfluorodecalin containing 0.5% w/v colloidal silicon dioxide and used for the test. The thixotropic pharmaceutical compositions were administered using drop sizes of approximately 12 µl, with examination of the eyes performed using gross and slit lamp techniques well known in the art.

While the 1% AGN 191053 composition was found to be slightly discomforting to the eye and slightly irritating to the conjunctiva, it proved to be neither toxic nor cytotoxic to the cornea. Further, all ocular reactions were found to be completely reversed within 24 hours following cessation of treatment. Conversely, the lower concentrations of AGN 191053 and the control without any drug produced no signs of discomfort or irritation in any of the eyes tested. Such results show that thixotropic pharmaceutical compositions of the present invention may be used for the repeated administration of selected compounds to the eye over prolonged periods.

EXAMPLE 8

To confirm the lack of toxicity associated with the thixotropic compositions of the present invention, a Chinese hamster ovary (CHO) clonal assay was performed to measure the cytotoxic effects of CSD and perfluorodecalin on cell viability. As is well-known in the art, the CHO clonal assay is extremely sensitive and is often used to test pharmaceutical composition toxicity. Different cell populations were exposed to 0.5% w/v CSD in perfluorodecalin, and from 0.01% to 0.1% w/v AGN 191053 dispersed in a suspension of 0.5% w/v CSD in perfluorodecalin. Straight perfluorodecalin was used as a negative control with a three-hour exposure period for each formulation tested.

Neither the perfluorodecalin nor the CSD/perfluorodecalin formulations exhibited any chemical toxicity with respect to the CHO cells. Only the formulations containing AGN 191053, which is known to have some antimicrobial activity, produced any cell mortality. Yet, even at concentrations of 0.01% w/v AGN 191053, greater than 90% cell survival was observed. These results illustrate that the thixotropic drug delivery vehicles of the present invention have virtually no cellular toxicity.

The pharmaceutical compounds used in the nonaqueous, low dose volume thixotropic compositions of the present invention can be prepared through a variety of methods known to those skilled in the art. Exemplary methods for preparing drugs or drug-associated microparticulates include grinding or milling mixtures of an appropriate polymer, therapeutic, or diagnostic drug. Alternative methodologies include grinding or milling the polymer to form microparticulates and subsequently absorbing the drug of choice into the microparticulates so produced. Microencapsulation techniques in which emulsions of the polymer and therapeutic or diagnostic compound are coacervated to precipitate the polymer and encapsulate the compound also can be used to form erodible microcapsules for use in the present invention.

Contributing to the economies of the present invention, the thixotropic pharmaceutical compositions may be prepared by techniques well-known in the art for formulating suspending aids in a liquid carrier. The amount of drug or drug-associated particulate suspended in the liquids of the present invention depend upon the dose configuration and the desired dose volume. For single dose units packaged in dropper style delivery systems, the volume ratio of carrier liquid to drug or polymeric microparticulate ranges from about 99.5 to about 5.0. Volume ratios for packaging configurations designed for multiple uses typically range from about 99.9 to about 3.0 liquid carrier to drug or microparticulate. As previously indicated, it is contemplated that pharmaceutical concentrations may range up to 50% w/v. Yet, preferably, the concentration of suspended drug or drug-associated microparticulate to nonaqueous carrier liquid will range from approximately 0 to 20% w/v and more preferably from 0.01% to 10%. Those skilled in the art will appreciate that these concentrations may be appropriately adjusted to adapt to the intended applications, target sites and pharmaceutical compounds utilized in accordance with the teachings of the present invention.

As an added benefit, the thixotropic pharmaceutical compositions of the present invention can be packaged for multi or single dose use. The availability of the option for multidose packaging is a significant advantage over single dose or unit dose packaging which is required for many prior art hydrolytically labile pharmaceutical compositions. Single dose packaging is more costly and many users prefer the convenience of, for example, large volume eye dropper delivery designs for multidose applications.

Whichever form of packaging is selected, the present invention is particularly well-suited to instillation in sensitive or easily damaged target sites and where the prevention of unwanted biological growth is critical. Unlike aqueous based pharmaceutical compositions which will support the growth of bacteria if preservatives are not used, the sterile pharmaceutical compositions of the present invention have bacteriostatic properties. These bacteriostatic properties make it possible to provide pharmaceutical compositions without added preservatives and the associated possibility of attendant side effects. This is particularly advantageous for users of ophthalmic preparations who exhibit a sensitivity to preservatives. Additionally, when the pharmaceutical compositions of the present invention are packaged in multidose configurations, they can be sterilized once and then repeatedly opened and reused without the subsequent growth of harmful organisms in the liquid carrier. The following example is illustrative of the inherent antimicrobial properties of the thixotropic pharmaceutical compositions of the present invention.

EXAMPLE 9

Microbiological testing of CSD/perfluorodecalin formulations was performed using a modified preservative efficacy test to demonstrate that the nonaqueous nature of the formulations of the present invention make them resistant to microbial growth. Formulations of 0.5% w/v CSD in perfluorodecalin and 0.3% w/v AGN 191053 dispersed in a suspension of 0.5% w/v CSD in perfluorodecalin were used in the testing procedures along with a perfluorodecalin control. Three common pathogenic microorganisms, S.aureus, P.aeruginosa and A.niger were inoculated in each of the formulations as dry pulverized lyophils at population densities of $10^6$. Different samples of the inoculated formulations were stored at 37° C. ambient humidity and 37° C., 85% relative humidity for 28 days. Samples from each inoculated formulation were pulled at 1, 4, 7, 14, 21 and 28 days to measure the amount of microbial contamination.

All of the tested samples passed the U.S.P. preservative efficacy test criteria. For bacteria, this standard is a minimum 3 log reduction of survivors by day 14 and stasis through day 28. For molds and yeasts, stasis through days 14 and 28 is the standard. This study shows that the compositions of the present invention are selfpreserving and can therefore be used in a multidose configuration without the addition of supplementary preservatives. Further, the results demonstrate that, in a high humidity environment, CSD in perfluorodecalin will not absorb a sufficient amount of water to support microbial growth or degrade incorporated hydrolytically labile pharmaceutical compounds. Accordingly, as the compositions of the present invention are not subject to biodegradation, their prolonged storage following exposure to microorganisms during use will not adversely affect their stability.

Preferably, the low volume, thixotropic pharmaceutical compositions of the present invention are finally packaged in sterile condition. This may be achieved through formulation procedures utilizing sterile fill methods and heat or gamma irradiation techniques to obtain a sterile product. One exemplary approach to producing a sterile thixotropic pharmaceutical composition may be used when the incorporated drug is to be associated with a polymeric particulate, and the desired microparticulate size is obtained with wet milling procedures employing a nonaqueous liquid carrier. Such a procedure includes sterilizing the drug/polymer stock powder mixture using a suitable sterilizing method such as heat or gamma irradiation, and sterile filtering the selected perfluorocarbon or fluorinated silicone. The sterile drug/polymer stock powder is then aseptically combined with the sterile nonaqueous liquid carrier and the mixture is wet milled until the desired particle size is reached. The final product is then aseptically filled into the desired package configuration.

Another procedure for obtaining sterile thixotropic pharmaceutical compositions of the present invention includes dry milling drug/polymer stock to the desired particle size followed by sterilizing the resulting drug-associated microparticulates. The sterile dry powders are then aseptically added to a previously sterile filtered perfluorocarbon or fluorinated silicone.

The following additional nonlimiting examples are illustrative of exemplary methods for formulating the sterile thixotropic pharmaceutical compositions of the present invention.

EXAMPLE 10

Aseptic formulation of thixotropic pharmaceutical compositions was conducted in accordance with the teachings of the present invention as follows. Various drugs in their salt forms, including levo-bunolol HCl, sodium cephazolin, AGN 191053, sodium flurbiprofen, AGN 190342, dipivalylepinephrine HCl, ofloxacin, prednisolone acetate, timolol, and sodium cromoglycate were air jet milled to a particle size less than 10 µm. Following the sizing operation, each individual drug was divided into lots, which were then placed in an atmosphere of either argon or air. Each lot was then sterilized using 1.0 or 2.5 Mrad of gamma radiation applied to the lots of each drug under argon or air. Concomitantly, colloidal silicon dioxide was sterilized using dry heat while perfluorodecalin was sterile filtered. The three components were then combined aseptically and blended using a high shear dispenser. The thixotropic pharmaceutical compositions were then analyzed by chromatographic techniques to determine the effect of gamma radiation on the stability of the ten drugs sterilized either in air or in the argon environment. No more than 5% activity was lost for any of the ten drugs sterilized as described above. Further, no biological growth or settling was observed in any of the pharmaceutical suspensions prepared in this manner.

To further demonstrate the ease of formulation and manufacture of commercial products utilizing the compositions of the present invention, packaging operations were carried out using standard equipment and well-known techniques. The following example is illustrative of the ease by which the present invention may be adapted for use with standard manufacturing technology.

EXAMPLE 11

A thixotropic pharmaceutical composition comprising 0.3% w/v AGN 191053 and 0.5% w/v colloidal silicon dioxide was sterilized using radiation in air as outlined in Example 10. Following the batch dispersion of the CSD and drug in the nonaqueous liquid carrier, the thixotropic composition was dispersed in 185 ophthalmic bottles, using standard filling techniques. Neither antistatic devices nor continuous stirring was used during the filling operation. Bottles were collected from the beginning, middle and end of the filling procedure and weighed and assayed for AGN 191053 content. The results of these observations are presented in Table 2 immediately below.

TABLE 2

|  | Weight | AGN 191053 Assay |
|---|---|---|
| Bottles: | 76 | 15 |
| Range: | 1.86–2.05g | 98–101.5%* |
| Average: | 2.00   g | 99.5%* |
| Std. dev.: | 0.03 | 1.1 |
| % RSD: | 1.6 | 1.1 |

*% of assayed AGN 191053 content prior to filling

Examination of the volumes in the table above shows that the fill volumes were within 1.6% RSD of the target weight (2.00 g) and the drug content was within 1.1% RSD of the target value of 0.3%. No phase separation or settling was observed in the batch thixotropic preparation during the filling procedure or in the filled bottles over time.

As will be appreciated by those skilled in the art, the exemplary perfluorocarbon and fluorinated silicone liquids used in the pharmaceutical compositions of the present invention provide unique chemical and physical properties which make them particularly well-suited for use as nonaqueous liquid carriers for polymeric drug delivery vehicles. More particularly, they are chemically and physically stable. The presence of suspending aids provides for the formation of a uniform suspension of the selected pharmaceutical compound in the nonaqueous liquid carrier regardless of whether the incorporated drug is in a salt form or associated with a polymeric microparticulate or microcapsule. Stable suspensions in turn contribute to the ability to deliver a consistent, low volume dose regimen over the life of the thixotropic pharmaceutical composition. Thus, the selected pharmaceutical compound, whether in a salt form or associated with a polymeric particulate, may be suspended in the nonaqueous liquid carriers for extended periods of time without undesirable phase separation or unwanted interactions between the carrier and the pharmaceutically active agent.

In addition to these enhanced liquid storage properties, the pharmaceutical compositions produced in accordance with the teaching of the present invention also have unexpectedly improved shelf-lives when compared with pharmaceutical compositions stored in a sterile, dry state. It is believed that the hydrophobic nature of the compositions precludes small amounts of oxygen and moisture from gaining access to the incorporated drugs. Accordingly, they remain viable and pharmaceutically active for an extended period of time. This is supported by the results of Example 9 where it was shown that the nonaqueous liquid carriers prevented the normally hygroscopic CSD from adsorbing enough water to reduce the activity of AGN 191053.

The following example further illustrates the enhanced shelf life and prolonged stability of exemplary thixotropic pharmaceutical compositions produced in accordance with the teachings of the present invention.

EXAMPLE 12

To determine the pharmaceutical and conformational stability of the compositions of the present invention, the bottles filled in Example 11 were divided, and one lot was stored at 30° C. in ambient humidity while the other lot was stored at 37° C. in 85% relative humidity. The bottles all contained approximately 2 g of a thixotropic pharmaceutical composition comprising 0.3% w/v AGN 191053 and 0.5% w/v colloidal silicon dioxide suspended in perfluorodecalin. The bottles were stored for 18 days with intermittent sample analysis consisting of drop size determination and drug content. The procedure used to determine drop size was gravimetric with each bottle being gently inverted 5 times prior to dispensing. The bottle was held 90° from horizontal and depressed gently until a drop formed and fell onto a tared weigh paper. The weight was recorded and converted to volume using the specific gravity of perfluorodecalin or 1.93 g/ml. The ophthalmic bottle used was a 3 ml Wheaton bottle, having a Wheaton 8 mm 0.02 tip. The number of dispensed drops for each data point was no less than 25. Results of the study are shown in Table 3 immediately below.

TABLE 3

| DROP SIZE FROM 3 mL WHEATON BOTTLE | | |
|---|---|---|
| Day | 30° C. | 37° C. @85% rel.hum. |
| 1 | — | 6.3 |
| 2 | 6.6 | 6.8 |
| 3 | 6.4 | 6.5 |
| 4 | 6.3 | 6.6 |
| 8 | 6.5 | 6.5 |
| 9 | 6.7 | 6.5 |
| 10 | 6.6 | 6.7 |
| 12 | 6.7 | 6.8 |
| 15 | 6.8 | 6.9 |
| 16 | 6.8 | 6.7 |
| 17 | 6.2 | — |
| 18 | 6.9 | — |
| Mean (μL) | 6.6 | 6.7 |
| Std Dev | 0.2 | 0.2 |

Following the determination of drop size, the thixotropic pharmaceutical compositions from both storage lots were analyzed to determine the concentration of remaining AGN 191053, using chromatographic techniques well-known in the art. The concentration was normalized and then compared to the observed concentration at day two. The results, in terms of percent drug remaining, are presented immediately below in Table 4.

TABLE 4

| NORMALIZED CONCENTRATION OF AGN 191053 IN DROPS FROM 3 Ml WHEATON BOTTLE | | | |
|---|---|---|---|
| Time (days) | 30° C. | 37° C. | n |
| 2 | 100.0 | 100.0 | 5 |
| 8 | 90.2 | 91.4 | 5 |
| 9 | 91.5 | 96.1 | 5 |
| 15 | 88.5 | 93.0 | 40 |
| 16 | 87.9 | 86.3 | 5 |

As shown by the tables above, drop volume over time remained surprisingly consistent. Further, there was no statistical difference between the drop volume produced by samples stored at 37° C. and those stored at 30° C. Similarly, the change in drug concentration was relatively uniform with both sets of samples recording a concentration change of slightly more than 10% over 16 days. Such results, unobtainable using prior art drug delivery vehicles, graphically illustrate the stability and prolonged uniform drug dispersion and delivery provided by the thixotropic pharmaceutical compositions of the present invention in multidose form.

In contrast, prior art pharmaceutical compositions formed using hydrolytically labile pharmaceutical compounds generally cannot be suspended for long term storage in aqueous carriers. Normally, these vehicles are packaged and stored in the dry state in order to achieve reasonable shelf lives. Users of these compounds which are stored without the benefit of being suspended in a carrier liquid are inconvenienced by the necessity of having to suspend the pharmaceutically active agents in a sterile aqueous carrier just prior to delivery to the target site.

This pharmaceutical stability and lack of phase separation associated with the present invention is especially important when the incorporated drug is hydrolytically labile or an unstable prodrug. As those skilled in the art will appreciate, hydrolytically labile compounds are characterized by their ability to physically or chemically erode in an aqueous environment. This erosion occurs over a period of time by any of a number of different processes such as enzymatic degradation, hydrolysis, or solubilization in response to contact with an aqueous physiological environment. Thus, when a hydrolytically labile compound such as a drug or polymeric particulate is placed in the ocular environment, it will erode in a manner that results in the sustained release or delivery of the drug to the eye. The formation of such sustained release pharmaceutical compositions having prolonged shelf lives would be impossible using prior art aqueous carriers as, assuming they survive storage, the particulates would rapidly be flushed or washed from the eye providing low bioavailability.

Significantly, the unique stabilizing properties of the compositions of the present invention also provide for the use of novel prodrug chemistry. The administration of these highly unstable, hydrolytically labile pharmaceutical compounds was essentially impossible using the prior art aqueous delivery vehicles. Yet, the thixotropic properties and nonreactive nature of the nonaqueous fluorinated compositions allow the incorporation of particularly efficacious prodrug forms of the selected pharmaceutical compound. Using the compositions of the present invention, the unstable prodrug may be stored in its most potent state until activated by the aqueous environment of the target site. The use of these potent drug precursors further reduces the amount of drug needed to provide an adequate therapeutic response thereby reducing the dosage and/or the frequency of administration.

The following nonlimiting examples illustrate the pharmaceutical stability of the present invention with respect to prodrugs as contrasted to prior art aqueous drug delivery vehicles.

EXAMPLE 13

A direct comparison of retained pharmaceutical activity was undertaken using the thixotropic compositions of the present invention and prior art aqueous vehicles. More particularly, the pharmaceutical compound AGN 191053, an unstable prodrug of isopilocarpine lactam, was sized using an air jet mill and sterilized using a 1.0 Mrad of gamma radiation, according to the protocol of Example 10. Samples of the sterilized drug were then formulated as aqueous solutions having different pH values, as well as a thixotropic composition in accordance with the teachings of the present invention, a dispersion of 0.5% w/v CSD in perfluorodecalin used to suspend the pharmaceutical compound. All formulations had the same initial concentration of drug. As a control, samples of the sterilized pharmaceutical compound were maintained in a dry state at elevated temperatures. The drug content of the various formulations was monitored for a period of two months. Results of this study, along with the specific physical parameters employed, are shown in FIG. 7.

Figure 7:
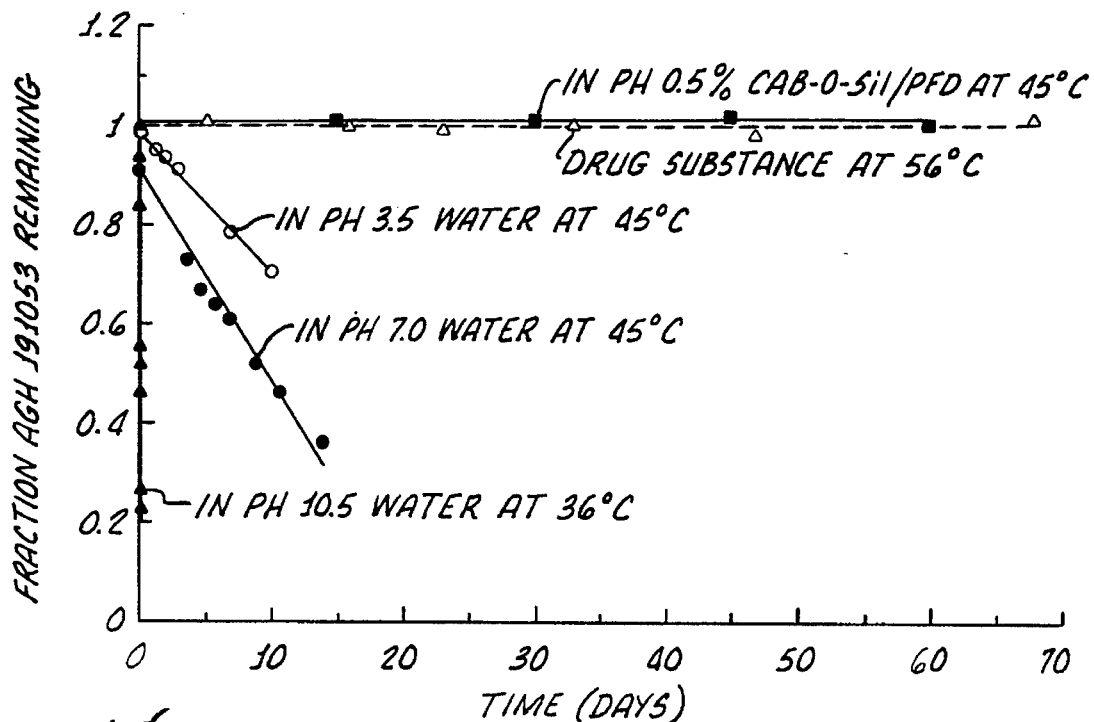
Figure 8:
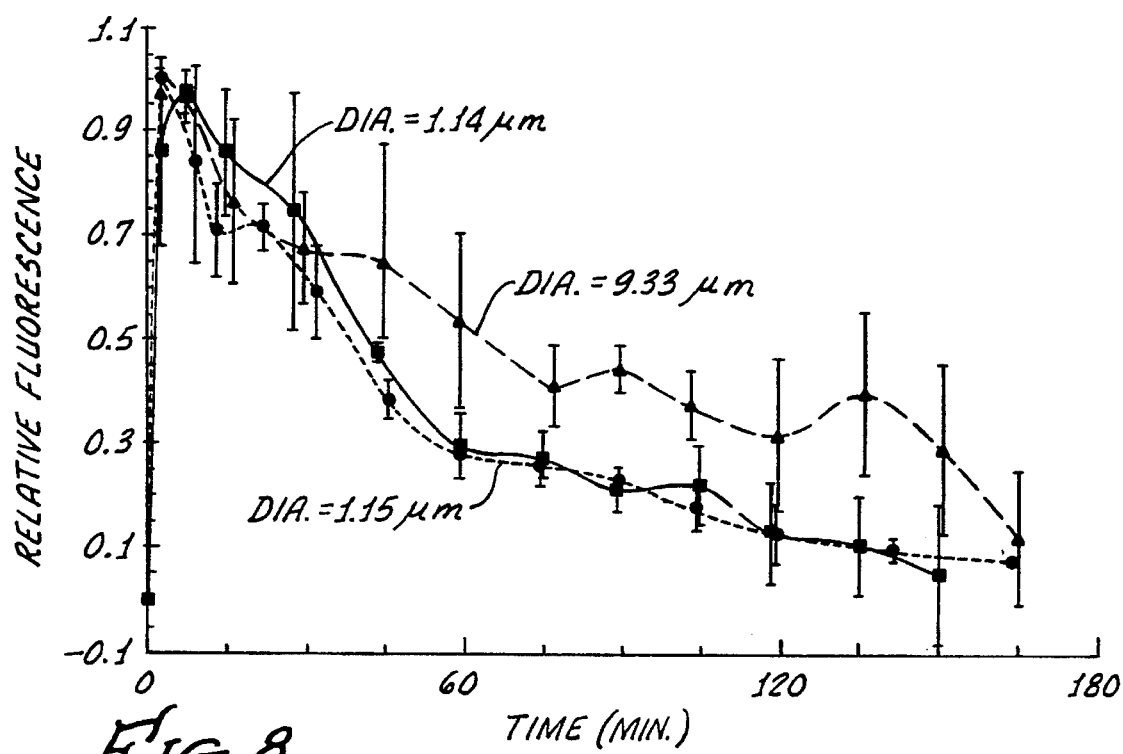

An examination of the curves represented in FIG. 7 shows that the prodrug of isopilocarpine lactam, AGN-191053, rapidly degraded when subjected to elevated temperatures in aqueous solutions. More specifically at pH 10.5 and 36° C., the measurable drug concentration was reduced below 20% almost immediately. Similarly, in aqueous solutions at pH 3.5 and pH 7, both at 45° C., drug concentrations were substantially reduced within 10 to 15 days. In sharp contrast, the drug concentration in the CSD/perfluorodecalin composition, made in accordance with the teachings of the present invention, showed no degradation for a period of almost two months at 45° C. Further, no phase separation or settling of the suspended drug was observed in the thixotropic pharmaceutical composition. This substantial elimination of drug degradation using such an unstable prodrug form of the compound graphically illustrates the enhanced pharmaceutical stability and extended shelf lives provided by the nonaqueous thixotropic compositions of the present invention.

EXAMPLE 14

To confirm the results of Example 13, an additional accelerated stability study was run on different formulations of thixotropic pharmaceutical compositions containing AGN 191053. Two formulations, both containing 0.3% w/v of the unstable prodrug were produced and subjected to elevated temperatures at different humidities. One formulation consisted of 1.0% w/v CSD in perfluorodecalin while the other consisted of 0.5% w/v CSD in perfluorodecalin. Both thixotropic pharmaceutical compositions were aliquotted into three lots, which were then stored at 30° C. ambient humidity, 37° C. 85% humidity, and 45° C. ambient humidity, respectively. Over a period of two months, no measurable degradation was observed in any of the formulations. Further, as observed in other studies, no settling or phase separation was reported for any of the samples. These results show that the present invention provides both conformational and pharmaceutical stability under widely divergent storage conditions.

The beneficial delivery characteristics of the high efficiency thixotropic pharmaceutical compositions are produced, in part, by the physical properties of the fluorinated liquid carriers. Following the breakdown of the thixotropic network due to the application of stress, the compositions of the present invention exhibit flow characteristics similar to pure fluorocarbons or fluorinated silicone liquids. That is, the properties of the nonaqueous liquid carriers dominate the thixotropic compositions upon breakdown of the network. Upon disruption of the network, the thixotropic compositions may be consistently delivered in low dose volumes of 10 µl or less using standard dropper delivery systems. More specifically, the high densities (typically greater than 1.2) and low surface tensions of perfluorocarbon and fluorinated silicone liquid carriers allow the delivery of dose volumes as low as 1 to 3 µl. The human ocular tear film is capable of accommodating volumes of only about 7 to 10 µl. Thus, the ability to deliver small volumes to the eye, along with the inherent bioadhesion and thixotropic retention produced by the compositions of the present invention, results in little or no loss of drugs. In contrast, the prior art drugs are largely blinked away when the prior art 35 µl–50 µl volume oil or water liquid carrier delivery compositions are utilized to deliver pharmaceutical agents to the eye.

Table 5 illustrates the dramatic distinction between the physical characteristics of water and that of two perfluorocarbons, PFD and PPP. As previously discussed, the disruption of the three dimensional network permits thixotropic compositions formulated in accordance with the teachings of the present invention using PFD or PPP to essentially assume these same characteristics. Thus, until the CSD structure is reestablished, PFD or PPP based compositions formed in accordance with the teachings of the present invention may be used to deliver advantageously small volume eye drops. This low volume delivery contrasts sharply with aqueous delivery systems which are limited to forming drops in the range of 35 µl–50 µl due to the relatively high surface tension and low density of the water carrier.

TABLE 5

|  | Water | PFD | PPP |
|---|---|---|---|
| Molecular weight | 18 | 462 | 624 |
| Boiling point (°C.) | 100 | 142 | 215 |
| Refractive index | 1.333 | 1.31 | 1.33 |
| Density @ 25° C. (gms/mL) | 1.000 | 1.929 | 2.016 |
| Kin. viscosity @ 25° C. (cSt) | 1.00 | 2.9 | 8.0 |
| Heat of vaporization (g-cal/gm) | 539.0 | 16.1 | 15.9 |
| Specific heat @ 25° C. (g-cal/gm) | 1.00 | 0.22 | 0.27 |
| Surface tension @ 25° C. (dynes/cm) | 72.0 | 19.3 | 21.6 |

The following nonlimiting example is further illustrative of the highly efficient, low dose volumes provided by the thixotropic pharmaceutical compositions of the present invention.

EXAMPLE 15

Studies were conducted to determine the average drop size obtained using standard delivery systems and different formulations of thixotropic drug delivery vehicles. As with Example 12, drop size was determined by gravimetric measurements. In all studies, the formulations were gently inverted five times prior to dispensing, at which time the bottle was held at 90° from horizontal and depressed gently until a drop formed and fell onto a tared weigh paper. The weight was recorded and converted to volume using the specific gravity of perfluorodecalin (1.93 g/ml). While the number of measurements for individual formulations differed, no data point was based on less than 25 drops.

The first study included four formulations of CSD and levo-bunolol suspended in perfluorodecalin. Concentrations of levo-bunolol ranged from 0.25% w/v to 1% w/v while concentrations of CSD were either 0.5% w/v or 1% w/v. Approximately 3 ml of each formulation were placed in 6 ml cylinders and a standard ophthalmic dropper tip was used to dispense the drops. The component concentrations of the formulations and the average drop sizes obtained are detailed in Table 6 immediately below.

TABLE 6

| Formulation (CSD / 1-bunolol) | Mean Drop Size (µL) | Standard Dev. |
|---|---|---|
| 0.5 / 0.5 | 6.5 | 0.1 |
| 0.5 / 1.0 | 6.6 | 0.2 |
| 1.0 / 0.5 | 7.0 | 0.2 |
| 0.5 / 0.25 | 6.5 | 0.3 |

As shown above, concentrations of 0.5 and 1.0% w/v colloidal silicon dioxide in perfluorodecalin produced low drop volumes of between 6.5 and 7.0 µl when dispensed using a standard dropper tip. Further, the drop volumes obtained were remarkable consistent with relatively small standard deviations. The consistency observed emphasizes the homogeneous nature and conformational stability of the thixotropic compositions. Further, concentrations of levobunolol from 0.25% w/v to 1.0% w/v appeared to have little effect on the low drop volume obtained.

EXAMPLE 16

A second study was conducted using the same protocol to illustrate the fact that the same low dose volume may be obtained using a variety of dropper tips and different pharmaceutical compounds. More particularly, a suspension of 0.5% w/v CSD and 0.5% AGN 191053 in perfluorodecalin was formulated in accordance with the teachings of the present invention. 1 ml of the formulation was placed into a 3 ml cylinder and dispersed with a Wheaton 8 mm 0.037 tip. By using the gravimetric techniques described above, small drop volumes of 5.9 µl were produced with a standard deviation of ±0.2 µl. An experimental control of 0.5% w/v CSD dispersed in perfluorodecalin produced mean drop sizes of 5.2 µl with a standard deviation of ±0.2 µl. These low dose volumes compare favorably with the drop sizes obtained in the previous example using a different pharmaceutical compound and a different tip. Further, the inclusion of a pharmaceutical compound did not adversely affect the low volume dosage.

It must be emphasized that while low dose volumes are desirable and readily obtainable using the thixotropic pharmaceutical compositions of the present invention, drop size may be adjusted by altering the tip configuration or by using different nonaqueous carriers. Accordingly, drop volumes on the order of 20 μl or larger are also contemplated as being within the scope of the present invention if warranted by the dosing requirements of an incorporated pharmaceutical compound or wetting agent.

Other beneficial characteristics of the pharmaceutical compositions of the present invention are derived from their ability to operate in the ocular environment with minimal vision disruption. As shown in Table 5 above, the nonaqueous carriers utilized in the pharmaceutical compositions of the present invention have refractive indices which are very close to that of water. What is more, these nonaqueous liquid carriers are immiscible with both the lipid layer and the aqueous layer of the ocular tear film. This immiscibility reduces disruptive interaction with the tear film layers. Additionally, the small drop volume results in the substantial elimination of the vision perturbation commonly associated with the use of current nonaqueous pharmaceutical carriers such as mineral oils.

As an added functional benefit, the thixotropic drug delivery vehicles of the present invention rapidly return to their relatively viscous resting state following administration. As previously discussed, this increase in viscosity is due to the rapid reformation of the three dimensional network as the finely dispersed particles of the suspending aid reorient themselves in the liquid carrier and bond to produce an aggregate network. As those skilled in the art will appreciate, any drug particulates, polymeric microparticulates or microcapsules incorporated in the thixotropic composition will be entrapped in the resulting visco-elastic matrix or network promoting extended localized retention.

As discussed above, the bioadhesive properties of the thixotropic compositions may be exploited by selecting hydrolytically resistent salts of the incorporated pharmaceutical compound which provide sustained dissolution following administration. Accordingly, the compositions of the present invention can be tailored to produce drop instillable drug delivery systems which will remain in the eye or at the target site for times ranging from fractions of an hour to ten hours or more. Preferably retention times can be produced ranging from two to six hours.

This prolonged drug retention and the concomitant increase in drug efficiency are illustrated in the following nonlimiting examples.

EXAMPLE 17

To graphically illustrate the enhanced drug bioavailability which may be achieved with the low dose volumes of the present invention, studies were performed to demonstrate the prolonged retention of particulates at the site of administration. Specifically, suspensions of 0.25% w/v fluorescein labeled latex particles were administered to the eyes of rabbits in 1% w/v CSD dispersed in perfluorodecalin according to the teachings of the present invention. Three different particulate sizes were tested while the thixotropic composition was administered in a low dose volume of 8 μl. As controls, the same particulates were administered as a prior art large volume aqueous suspension of 35 μl. The results are graphically represented in FIG. 8.

As illustrated in the graph of FIG. 8, the precorneal retention half-life for the three different particulates tested was approximately one hour when administered using the thixotropic compositions of the present invention. In sharp contrast, when the same particulates were administered as a prior art large volume aqueous suspension, all of the particulates drained from the eye along with the liquid carrier in less than two minutes. Accordingly, these prior art vehicles do not even show up in the time scale of FIG. 8. This unexpectedly long particulate retention provided by the thixotropic properties of the present invention compositions combined with the associated bioadhesion of the particles to the mucin, may be used to selectively position hydrolytically resistent compounds resulting in enhanced, localized drug bioavailability. Moreover, while polymer microparticulates were used for this study, equivalent localized retention may be obtained by using a less soluble free base form of any selected pharmaceutical compound which provides sustained dissolution.

EXAMPLE 18

To further demonstrate the drug retention capabilities of the present invention, radiolabeled micronized charcoal particles were administered to the eyes of rabbits using exemplary low dose volume nonaqueous thixotropic compositions and using prior art aqueous delivery vehicles. Micronized charcoal was labeled with Technetium-99m ($Tc^{99m}$) and formulated with colloidal silicon dioxide and perfluorodecalin to produce a thixotropic composition having a final concentration of 0.5% CSD and 1% charcoal. An aqueous solution containing 1% labeled charcoal was also formulated for use as a control with both formulations having activities of approximately 3 MBq per 8 μl dose volume. Each formulation was tested on six rabbits by administering a drop to the top of the scleral region of one eye. Using a positive displacement pipette, a drop volume of 8 μl was used to administer both formulations. Gamma scintigraphy was then used to monitor the presence of labeled charcoal in the corneal region, the inner canthus and the lacrimal duct.

The field of view of the monitoring apparatus was divided into 3 regions of interest or ROI's using predefined anatomical reference points. One of these regions corresponded to the area immediately surrounding the precorneal area while a second region centered on the inner canthus. A third region outlined the lacrimal duct of the rabbit. The monitoring apparatus could differentiate and keep track of counts originating from each region of interest. Values used to determine the percentage of labeled charcoal in a specific area were the number of counts originating from a particular region over a time frame of two seconds. The results of these measurements are presented in FIGS. 9A, 9B and 9C.

Figure 9A:
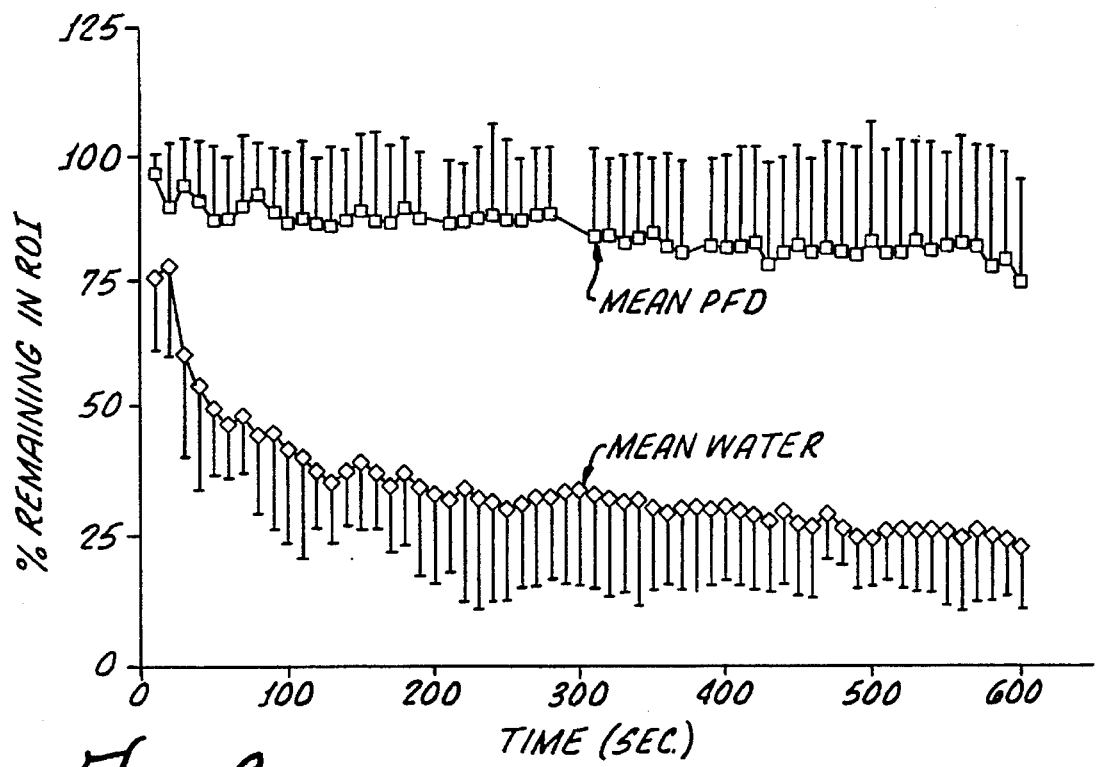

FIG. 9A is a graphical representation of the percentage of radiolabeled charcoal retained in the cornea over a period of approximately ten minutes following administration of the selected formulation. The percentage of charcoal remaining at the site is a function of the measured radioactivity divided by the radioactivity of the composition administered. When plotted, the curves show that the amount of charcoal retained in this region using the thixotropic composition remained at approximately 100% over the monitoring period. In sharp contrast, the corneal activity of the charcoal administered in an aqueous vehicle rapidly decreased to approach a baseline of approximately 25%.

Figure 9B:
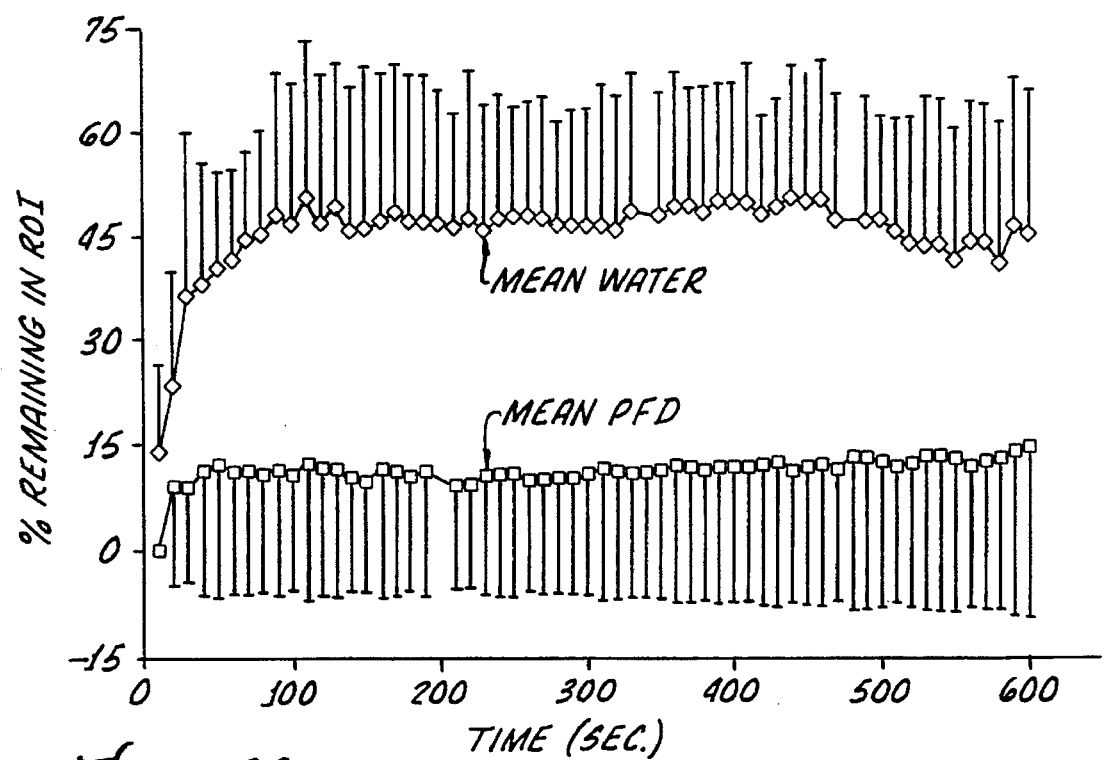
Figure 9C:
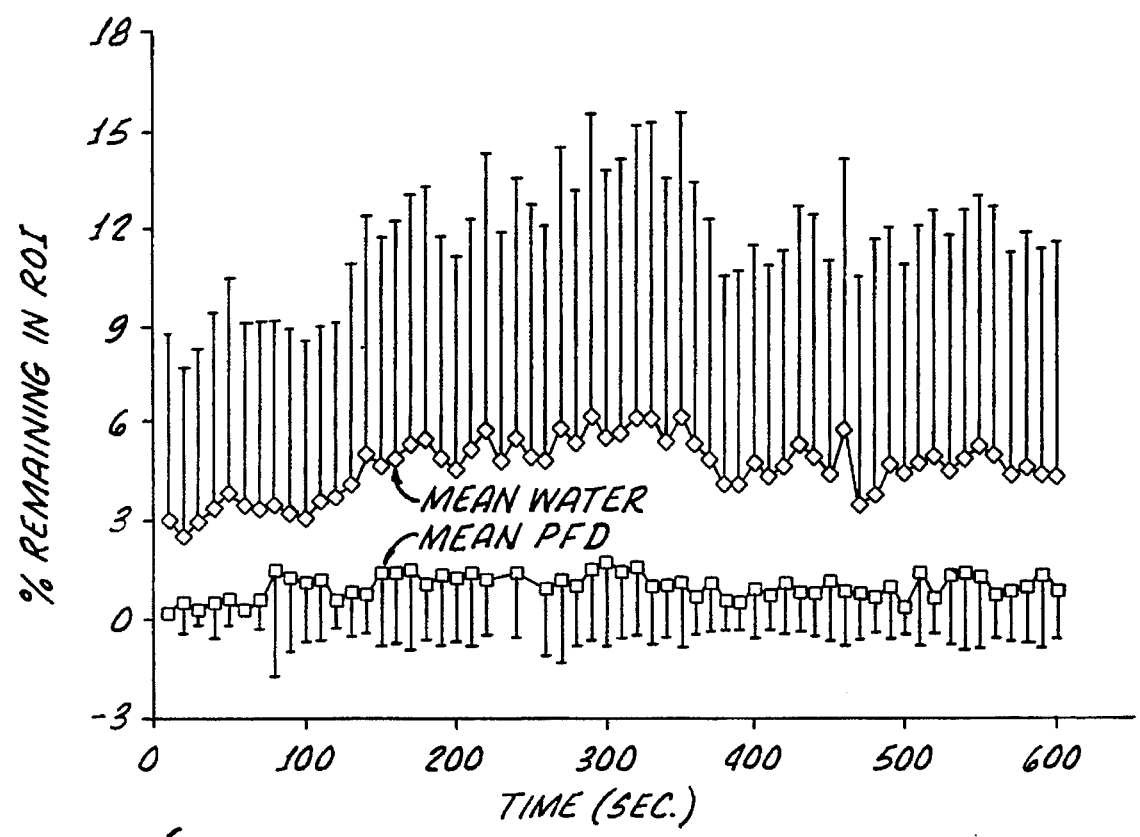

FIGS. 9B and 9C also illustrate the enhanced retention of drug at the target site when administered using the thixotropic compositions. More specifically, FIG. 9B is a graphical representation of the amount of labeled charcoal which migrated away from the corneal target site to the inner canthus of the rabbit eye. A much higher level of migration, well over 45% of the charcoal administered, was observed in with the aqueous based delivery system as compared to the relatively low levels of less than 10% seen with the nonaqueous thixotropic vehicles. These results are repeated in FIG. 9C where the amount of charcoal which has migrated to the rabbit lacrimal duct is displayed. This graph shows that approximately 5% to 10% of the charcoal administered using the aqueous vehicle travelled as far as the lacrimal duct within two minutes of installation. Conversely, when the nonaqueous thixotropic delivery vehicles of the present invention were used, almost imperceptible levels of the labeled charcoal are found in the lacrimal duct as long as ten minutes after installation. This lack of particulate migration graphically demonstrates the particulate retention and high localized bioavailability provided by the compositions of the present invention.

EXAMPLE 19

To further illustrate the enhanced particulate retention provided by the pharmaceutical compositions of the present invention and demonstrate their efficacy in a broad range of species, particulate retention studies were performed on human subjects. As in Example 18, micronized charcoal was labeled with Technetium-99m ($Tc^{99m}$) and formulated with colloidal silicon dioxide and perfluorodecalin to produce a thixotropic composition having a final concentration of 0.5% CSD and 1% charcoal. An aqueous solution of 1% labeled charcoal was used as a control with both formulations having activities of approximately 1 MBq per 7 μl dose volume. Each formulation was then administered to the cornea of the left eye of the human subjects using a positive displacement pipette. As in the experiment on rabbits gamma scintigraphy was then used to monitor the presence of labeled charcoal in the corneal region, the inner canthus and the lacrimal duct.

Essentially, the results obtained using human subjects paralleled those obtained in Example 18 using rabbits. When the labelled charcoal was administered in the thixotropic compositions of the present invention, the majority of the particulates were retained in the corneal region. In contrast, when the charcoal was administered using an aqueous carrier, the majority of the labelled particulates quickly migrated to the inner canthus and lacrimal duct of the subjects. After two hours approximately 40% of the labelled charcoal was retained in the corneal region when the particulates were administered in a PFD/CSD suspension compared to a less than 10% retention rate when administered using water. Conversely, almost twice as much labelled charcoal was found in the inner canthus and lacrimal duct after two hours when the particulates were administered using water as when they were administered using the non-aqueous delivery vehicles of the present invention. Such data confirms the results demonstrated previously in rabbits while strongly supporting the applicability of using the present invention in a number of different species including man.

EXAMPLE 20

To more clearly demonstrate the enhanced particulate retention and corresponding decrease in non-specific drug migration provided by the present invention, radiolabeled charcoal was again administered to the eyes of rabbits and monitored using gamma scintigraphy. The protocol was the same as that used in Example 18 except that only one rabbit eye was used for each formulation.

Following administration of the labeled charcoal, radiation counts were collected from various regions of interest corresponding to those defined in Example 18. Instead of linearly graphing the remaining activity as done previously, an integrated, high resolution radiation contour map was constructed for each monitored time following administration. The maps, representative of the dispersion and relative concentration of the charcoal particles in the ocular environment, were produced by distinguishing the amount of radiation emitted from each point in the ocular system and characterizing the resultant values by color or shading. Maps of each particular time point are shown superimposed over a schematic ocular system of a rabbit in FIGS. 10 and 11.

More particularly, the radiation contour maps made following administration of the labeled charcoal using a prior art aqueous delivery vehicle are illustrated in FIGS. 10A, 10B, 10C and 10D. These figures correspond to time frames at 20 seconds, 50 seconds, 10 minutes and 38 minutes after administration of the charcoal particles. Similarly, FIGS. 11A, 11B, 11C, 11D, and 11E illustrate the relative concentration of the labeled charcoal at 50 seconds, 10 minutes, 19 minutes, 34 minutes and 135 minutes following administration in a thixotropic composition of the present invention.

In all Figures, the rabbit ocular region 20 includes a precorneal area 22, inner canthus region 24 and lacrimal duct 26. Superimposed on the rabbit ocular region 20 is the radiation contour map for each respective time interval measurement. The relative radioactivity observed for a coordinate is represented as low activity 32, medium activity 34, or high activity 36. These readings, when combined, provide visual conformation of the extended ocular residence time provided by the present invention.

Figure 10A:
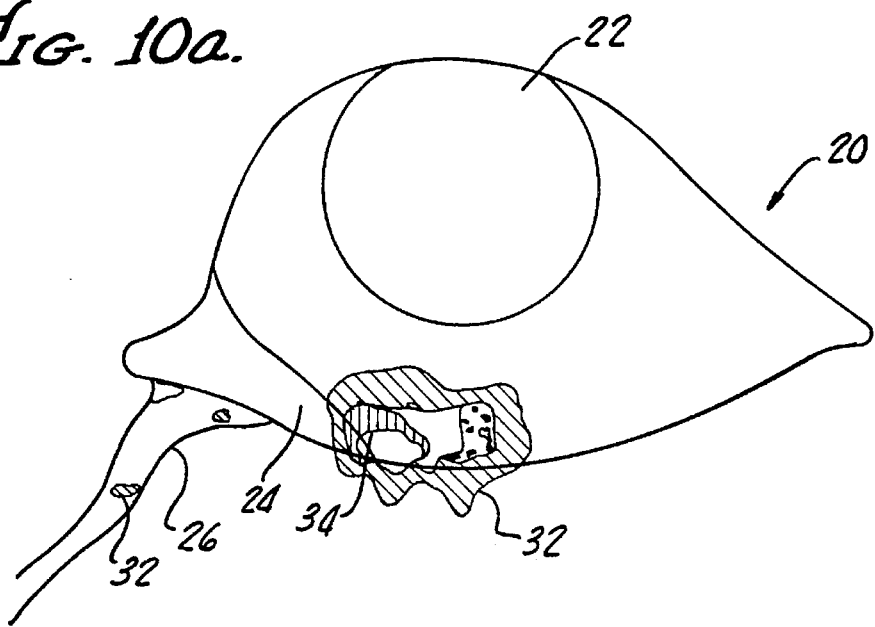
Figure 10B:
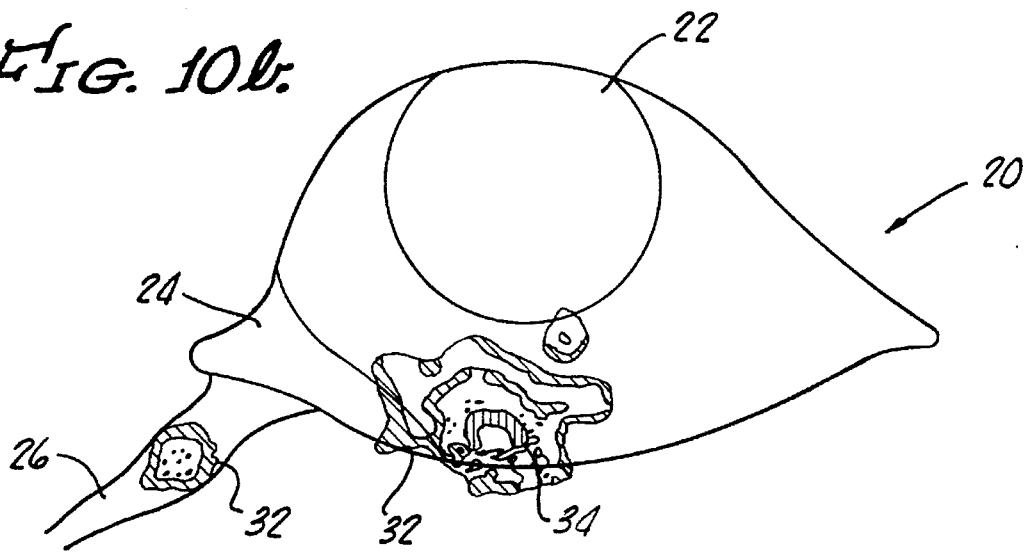
Figure 10C:
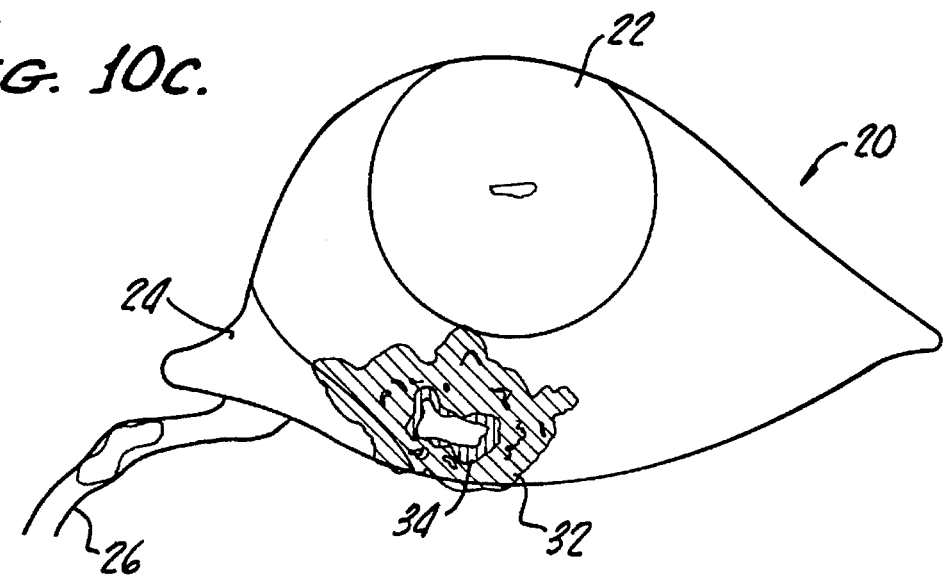
Figure 10D:
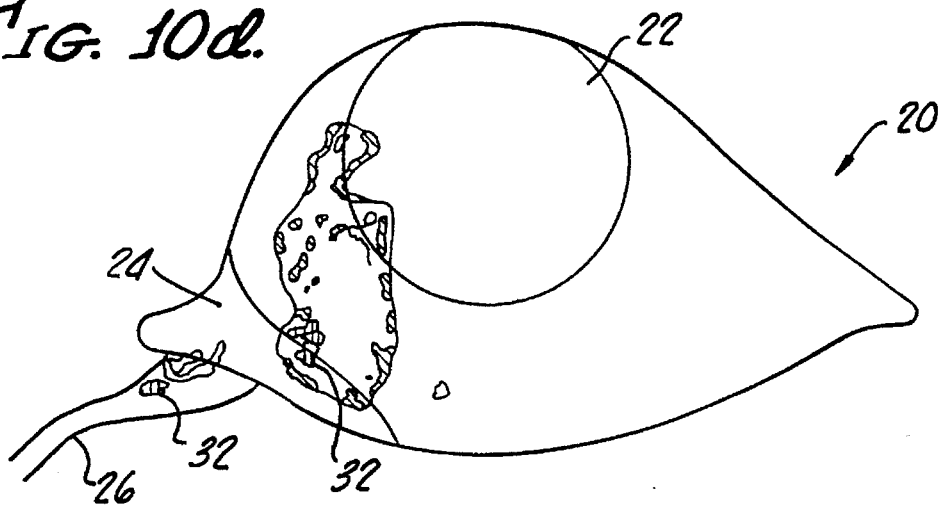

Both prior art and exemplary particulate compositions were administered to the precorneal area 22 of the rabbit ocular region 20 to initiate the measurement. An examination of FIGS. 10A, 10B, 10C and 10D shows that almost no radiation is detected within the precorneal area 22 following administration of the labeled charcoal in the aqueous vehicle. FIG. 10A shows that in as little as 20 seconds after administration the great majority of the particulates have migrated to the inner canthus 24 and show high activity 36 with an initial penetration into the lacrimal duct 26 showing low activity 32. This pattern is substantially repeated in FIGS. 10B and 10C with an increase in observed activity in the lacrimal duct 26 over time as the particles continue to migrate. 38 minutes after administration, the radioactive particles had essentially dissipated as shown in FIG. 10D leaving residual traces of low activity 32 and medium activity 34 from particulates deposited at the inner canthus 24 and lacrimal duct 26.

Figure 11A:
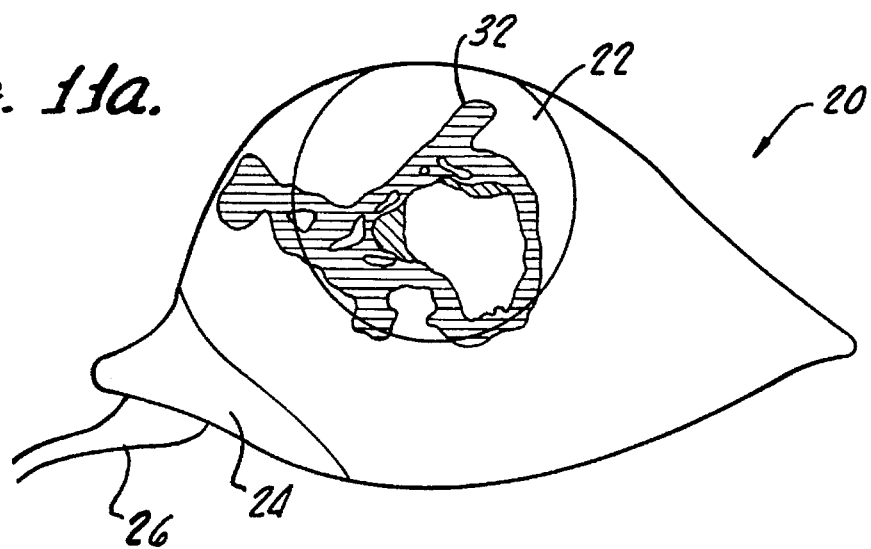
Figure 11B:
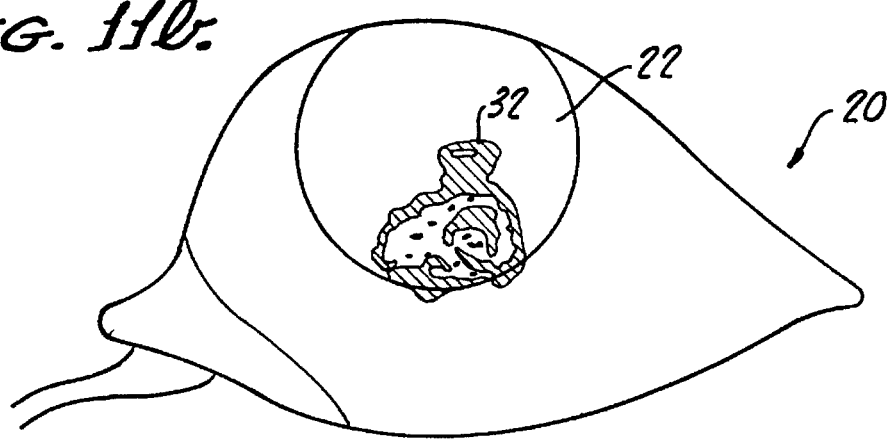
Figure 11C:
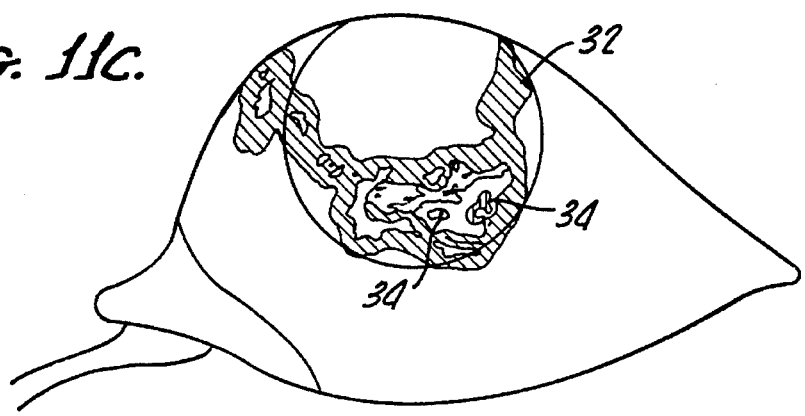
Figure 11D:
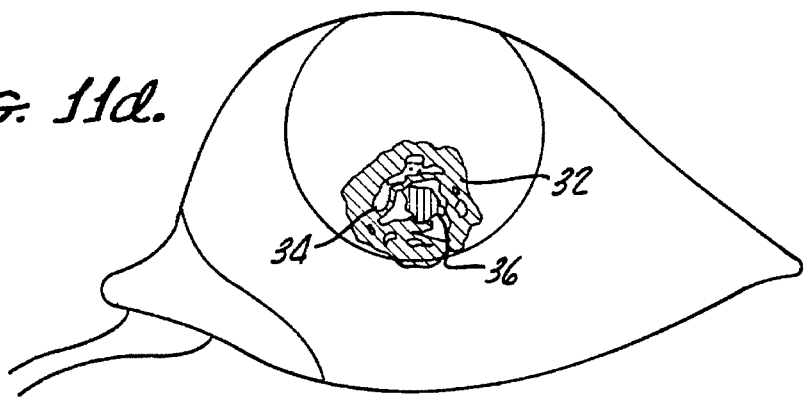
Figure 11E:
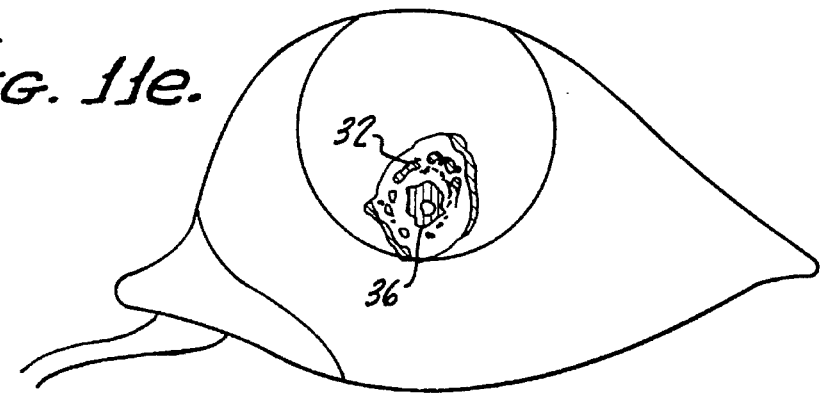

In sharp contrast, FIGS. 11A, 11B, 11C, 11D and 11E show that, upon administration of the labeled particles using the exemplary nonaqueous thixotropic delivery vehicle of the present invention, the recorded activity remained exclusively in the precorneal area 22. No detectible migration of the charcoal particulates to the inner canthus 24 or lacrimal duct 26 was observed despite monitoring the ocular region for well over two hours. Rather, FIG. 11A, generated at 50 seconds following administration, shows a collection of particulates at the lower edge of the precorneal area 22. FIGS. 11B and 11C further illustrate the selective retention of the labeled particulates in the mucin of the precorneal area 22. In FIG. 11D, generated at 34 minutes, the detectable activity was focused in a relatively small region at the bottom of precorneal area 22. Almost two hours later, at 135 minutes after administration, FIG. 11E shows that, while the measured activity has fallen off due to the half-life of the isotope, there has been almost no detectable movement in particulate location.

The following nonlimiting example further illustrates the improved drug delivery profiles, enhanced bioavailability and increased duration of pharmacologic activity provided by the superior retention capability of the present invention.

EXAMPLE 21

Three different concentrations of pilocarpine were formulated as prior art aqueous solutions and as exemplary nonaqueous thixotropic pharmaceutical compositions according to the teachings of the present invention. Specifically, aqueous solutions and nonaqueous suspensions of 0, 0.1%, 0.5% and 2% pilocarpine were formulated under sterile conditions. The nonaqueous drug suspensions were made using 0.5% CSD uniformly dispersed in perfluorodecalin. Both sets of formulations were administered to rabbit eyes in drop volumes of 8 µl using positive displacement pipettes. Changes in pupil diameter were monitored with three rabbits being used for each concentration of each formulation. The results of these measurements are graphically presented in FIGS. 12A and 12B. In particular, FIG. 12A illustrates the effects of the three different concentrations of isopilocarpine lactam administered using the nonaqueous vehicle while FIG. 12B illustrates equivalent data for the prior art solubilized aqueous pilocarpine.

Figure 12A:
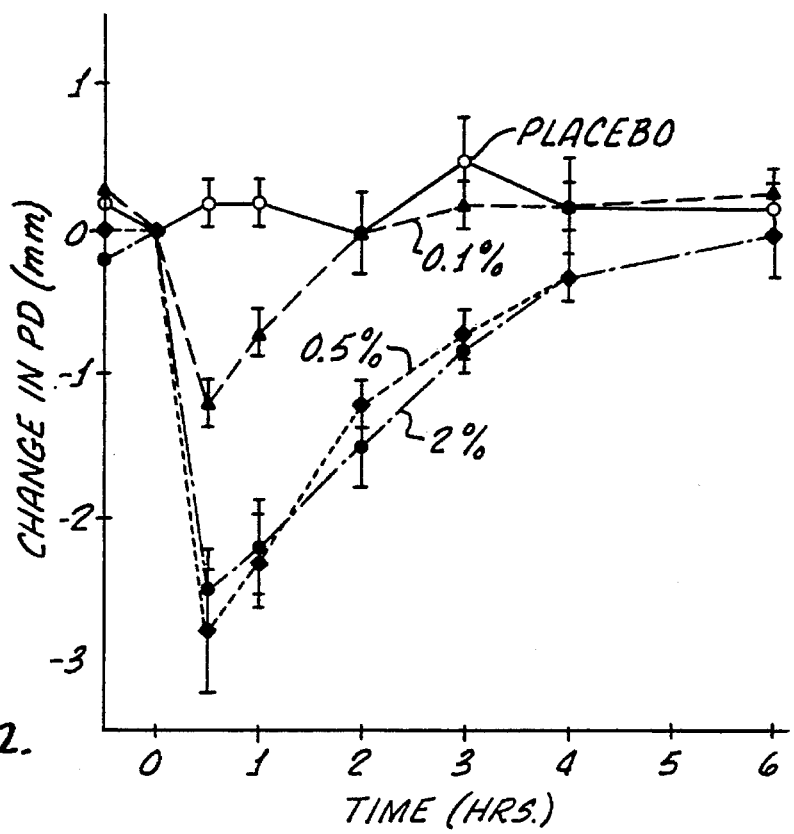
Figure 12B:
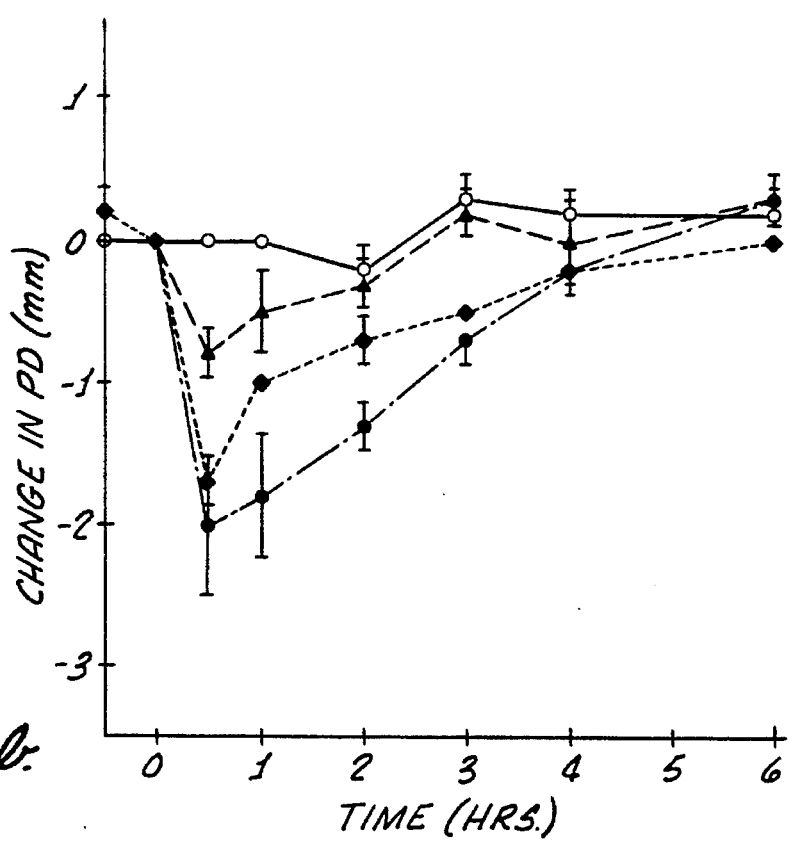

An examination of FIGS. 12A and 12B shows that, for equivalent drug concentrations, the nonaqueous thixotropic pharmaceutical compositions of the present invention produced a greater pharmaceutical effect, i.e. a reduction in pupil size, than did the prior art aqueous formulations. Moreover, while recovery periods were time dependent for both formulations, the nonaqueous formulation exhibited a prolonged recovery period indicating sustained drug bioavailability. These results demonstrate that the solubilized pilocarpine was rapidly flushed away or otherwise removed from the target site while the PFD/CSD suspended particulates of pilocarpine were deposited at the target site and slowly administered. This prolonged drug retention was facilitated by a combination of the thixotropic matrix at the surface of the eye and the bioadhesion of the drug particulates to the desiccated mucin produced by the present invention. Those skilled in the art will realize that the dissolution of the drug particulate and the corresponding drug delivery profile can be tailored in accordance with the teachings of the present invention by selecting a different salt form of the drug having increased or decreased aqueous solubility.

This effective localization of the drug, combined with the ability to incorporate more potent prodrug compounds, produces substantial reductions in systemic side effects. This higher bioavailability and associated increased efficacy allow much lower, yet pharmaceutically effective doses to be administered with the present invention compared to prior art compositions. This allows the thixotropic compositions of the present invention to produce therapeutic results comparable with prior art compositions even though the total dosage of the incorporated pharmaceutical compound can be reduced by approximately 70% to 80%. Combined with this dosage reduction, the ability of the low delivery volume nonaqueous thixotropic compositions of the present invention to substantially eliminate drug migration from the target site dramatically reduces undesirable side effects. Such a reduction of systemic side effects can be critical in a therapeutic setting and, accordingly, is an important benefit provided by the compositions and methods of the present invention.

EXAMPLE 22

Figure 13A:
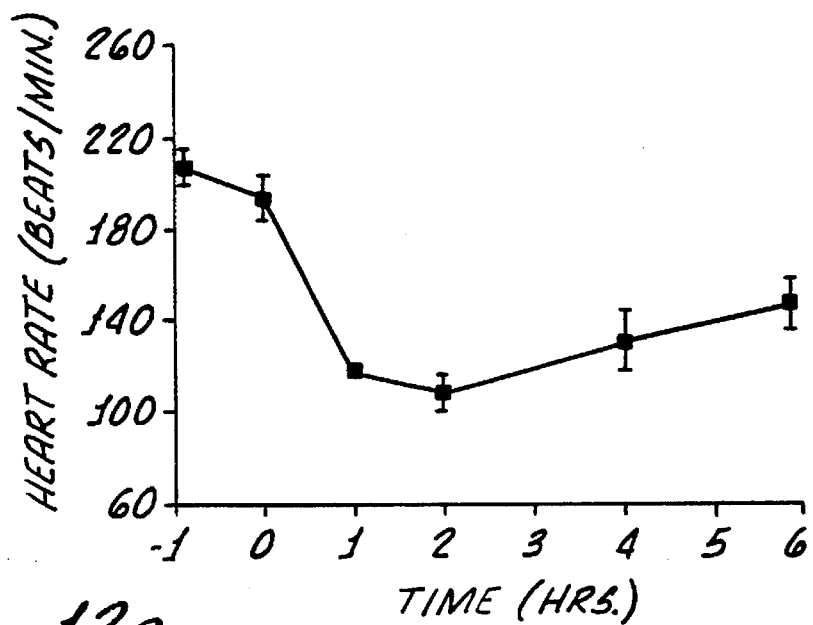
Figure 13B:
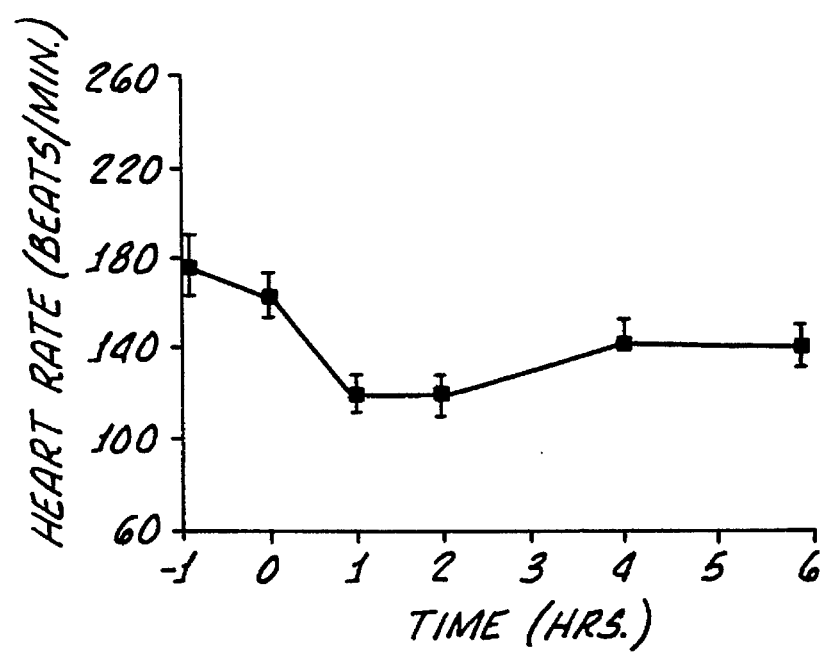

To illustrate the high localized drug bioavailability and correspondingly low systemic side effects of the present invention, a pharmacology study was conducted on conscious, glaucomatous monkeys. Formulations of 0.25% w/v levo-bunolol, used to reduce intraocular pressure in glaucoma patients, were administered as an aqueous solution and as a thixotropic pharmaceutical composition made in accordance with the teachings of the present invention. The monkeys were monitored for reductions in intraocular pressure, indicating the desired localized drug action, and for changes in heart rate, indicating undesirable drug migration away from the target site and into the systemic circulation. The thixotropic compositions were administered in low dose volume 8 µl drops while the aqueous formulations were administered in prior art drop volumes of approximately 35 µl. The effect of the different compositions on heart rate are shown in FIGS. 13A and 13B. FIG. 13A is the mean reduction in heart rate for the monkeys treated with the aqueous solution of the drug while FIG. 13B is the mean reduction in heart rate for the monkeys treated with the nonaqueous formulation.

The reduction in intraocular pressure was almost identical with respect to both formulations in spite of the fact that the actual dosage delivered using the CSD perfluorodecalin suspension of the present invention was only approximately 22% of that delivered using the prior art aqueous solution. More importantly, as evidenced by comparing FIGS. 13A and 13B the decrease in heart rate for the monkeys treated with the thixotropic pharmaceutical composition of the present invention was only 65% that of the monkeys treated with the prior art aqueous solution. These results explicitly illustrate the high localized bioavailability, reduced migration and lower nonspecific adsorption provided by the thixotropic pharmaceutical compositions of the present invention.

A demonstration of further advantages of the present invention with respect to undesirable side effects is provided in the following nonlimiting example.

EXAMPLE 23

Pharmacological studies were conducted on various formulations containing brimonidine to illustrate the high localized bioavailability and corresponding reduction of nonspecific systemic side effects provided by the present invention. The formulations containing brimonidine were prepared by mixing an appropriate amount of the dry form of the pharmaceutical compound with sterilized CSD. This mixture was then dispersed in perfluorodecalin where each formulation was vortexed briefly and sonicated for 45 minutes to ensure uniform dispersion of the CSD and suspended drug. As a control, an aqueous solution containing the same amount of drug was prepared. The final concentration of the brimonidine in both formulations was 0.1% w/v. The non-aqueous thixotropic compositions of the present invention were administered in a low dose volume of 8 µl, while the prior art aqueous control was administered in a volume of 50 µl. The drugs were administered to one eye of the rabbit with both eyes subsequently monitored for changes in intraocular pressure. Results of these measurements are shown in FIGS. 14A and 14B.

Figure 14A:
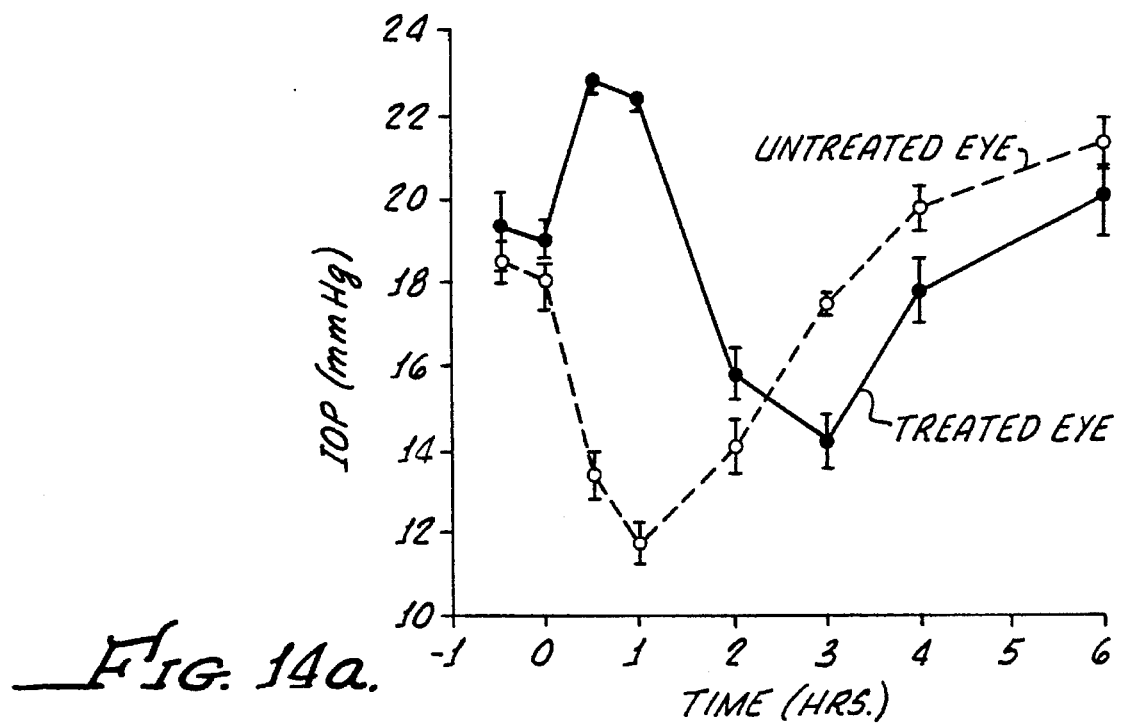
Figure 14B:
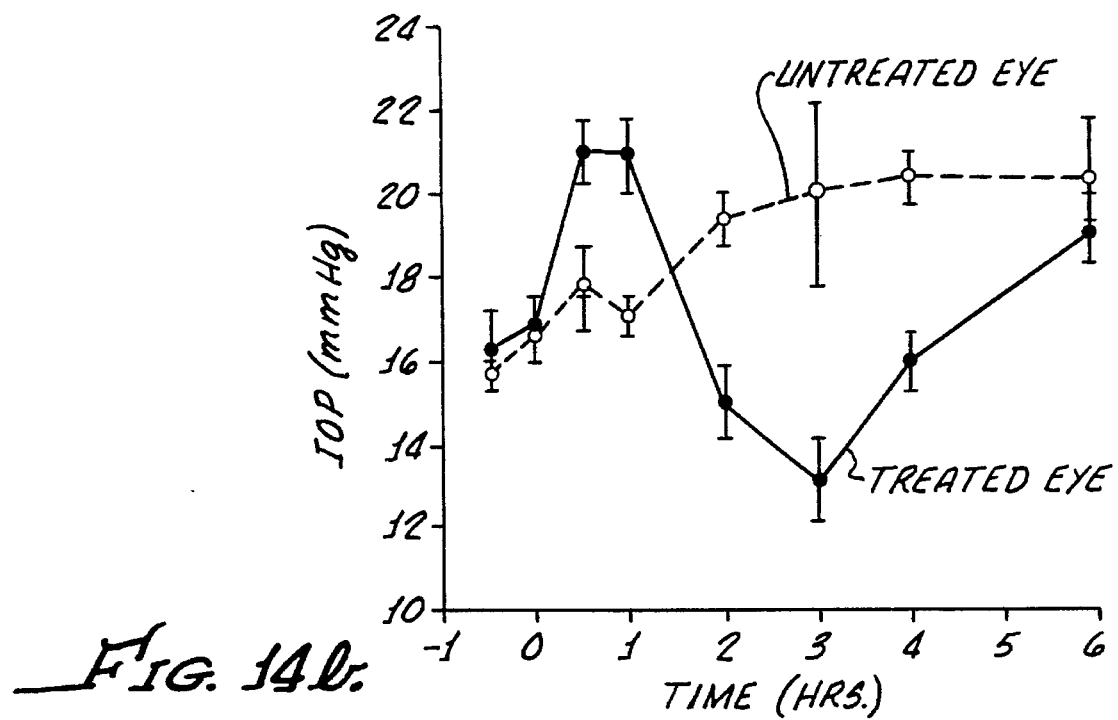

As seen in FIGS. 14A and 14B, despite the substantial relative reduction in drug dosage, the thixotropic pharmaceutical compositions of the present invention produced peak mean intraocular pressure reductions for the treated eye comparable to the much larger aqueous based prior art dosage. FIG. 14B also shows that the low dose volume thixotropic pharmaceutical compositions produced significantly less intraocular pressure response in the untreated eye when compared with the prior art aqueous control shown in FIG. 14B. The incorporation of the drug within the rapidly established visco-elastic network, along with the bioadhesion of the drug particulate, substantially reduced the nonspecific distribution associated with the aqueous delivery vehicle and as a result, reduced the systemic side effects associated with the prior art delivery vehicle.

Those skilled in the art will further appreciate that the present invention may be embodied in other specific forms without departing from the spirit or central attributes thereof. In that the foregoing description of the present invention discloses only exemplary embodiments thereof, it is to be understood that other variations are contemplated as being within the scope of the present invention. Accordingly, the present invention is not limited to the particular embodiments which have been described in detail herein. Rather, reference should be made to the appended claims as indicative of the scope and content of the present invention.

What is claimed is:

1. A method for delivering pharmaceutical compounds to the eye, said method comprising the steps of:
    providing a thixotropic pharmaceutical composition comprising a therapeutic or diagnostic compound incorporated in a substantially homogeneous dispersion of a suspending aid in a nonaqueous physiologically acceptable fluorinated liquid; and
    introducing a pharmaceutically effective amount of said thixotropic pharmaceutical composition to the eye.

2. The method of claim 1 wherein the concentration of said suspending aid is from approximately 0.01% w/v to approximately 20% w/v.

3. The method of claim 2 wherein the concentration of said suspending aid is from approximately 2% w/v to approximately 10% w/v.

4. The method of claim 1 wherein said suspending aid is selected from the group consisting of surfactants, dispersants, suspending agents and excipients.

5. The method of claim 1 wherein said suspending aid is selected from the group consisting of colloidal silicon dioxide and derivatives thereof.

6. The method of claim 1 wherein said therapeutic or diagnostic compound is associated with polymer particulates selected from the group consisting of microparticulates and microcapsules.

7. The method of claim 6 wherein said polymer particulates are fabricated from a hydrolytically labile polymer selected from the group consisting of poly(methylvinylether/maleic anhydride), polyfumaric acid/sebacic acid, collagen, gelatin, polyvinyl alcohol, methylcelluloses, polyorthoesters, polyglycolic acid, polylactic acid, polyvinylpyrrolidone, polysebacic acid anhydride, polycarboxyphenoxypropane anhydride, polyterephthalic acid anhydride, and polyphosphazine.

8. The method of claim 1 wherein said nonaqueous fluorinated liquid carrier is selected from the group consisting of perfluorocyclocarbons, nitrogen containing perfluorocyclocarbon, oxygen containing perfluorocyclocarbon, acyclicperfluorocarbons, nitrogen containing acyclic perfluorocarbon, and oxygen containing acyclic perfluorocarbon.

9. The method of claim 1 wherein said pharmaceutically effective amount of said thixotropic pharmaceutical composition is introduced in a low dose volume greater than about 1 microliter and less than 20 microliters.

10. The method of claim 9 wherein said low dose volume is about 6 microliters to about 12 microliters.

* * * * *